US012419745B2

(12) United States Patent
Giese et al.

(10) Patent No.: US 12,419,745 B2
(45) Date of Patent: Sep. 23, 2025

(54) DEVICES, SYSTEMS, AND METHODS FOR ADJUSTABLY TENSIONING ARTIFICIAL CHORDAE TENDINEAE IN A HEART

(71) Applicant: Boston Scientific Scimed, Inc., Maple Grove, MN (US)

(72) Inventors: Troy A. Giese, Blaine, MN (US); Christopher J. Koudela, New London, MN (US); James P. Rohl, Prescott, WI (US); Daniel Shuey, Pine City, MN (US); Larry M. Killeen, Elk River, MN (US); Joel T. Eggert, Plymouth, MN (US); Aaron Abbott, Columbia Heights, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 29 days.

(21) Appl. No.: 17/483,206

(22) Filed: Sep. 23, 2021

(65) Prior Publication Data
US 2022/0096235 A1   Mar. 31, 2022

Related U.S. Application Data

(60) Provisional application No. 63/085,390, filed on Sep. 30, 2020.

(51) Int. Cl.
*A61F 2/24*   (2006.01)

(52) U.S. Cl.
CPC .... *A61F 2/2457* (2013.01); *A61F 2220/0016* (2013.01); *A61F 2220/0075* (2013.01); *A61F 2250/0007* (2013.01)

(58) Field of Classification Search
CPC .............. A61F 2250/0007; A61F 2/2457
See application file for complete search history.

(56) References Cited

U.S. PATENT DOCUMENTS 5,702,397 A * 12/1997 Goble .................. A61F 2/0811
606/86 R
7,736,388 B2   6/2010 Goldfarb et al.
(Continued)

FOREIGN PATENT DOCUMENTS

GB         2581545 A  *  8/2020  ............. A61B 17/04
JP      2020503165 A       1/2020
(Continued)

OTHER PUBLICATIONS

International Search Report and Written Opinion for the International Patent Application No. PCT/US2020/040672, mailed Oct. 16, 2020, 14 pages.
(Continued)

*Primary Examiner* — Suba Ganesan
(74) *Attorney, Agent, or Firm* — Seager, Tufte & Wickhem, LLP

(57) ABSTRACT

Devices, systems, and method for adjusting and setting tension of an artificial chordae tendineae. The artificial chordae tendineae is coupleable between a leaflet clip and a tissue anchor. A locking assembly, through which the artificial chordae tendineae extends, is shiftable between a tension-adjusting configuration, in which the artificial chordae tendineae is movable to adjust tension on the leaflet, and a tension-setting or locked configuration, in which the artificial chordae tendineae is inhibited or prevented or locked against moving with respect to the locking assembly to set or fix tension on the leaflet.

20 Claims, 15 Drawing Sheets

(56) References Cited

U.S. PATENT DOCUMENTS

| | | | |
|---|---|---|---|
| 8,252,050 B2 | 8/2012 | Maisano et al. | |
| 8,303,622 B2 | 11/2012 | Alkhatib | |
| 9,681,864 B1 | 6/2017 | Gammie et al. | |
| 9,877,833 B1 | 1/2018 | Bishop et al. | |
| 10,136,993 B1 | 11/2018 | Metchik et al. | |
| 2006/0276890 A1 | 12/2006 | Solem et al. | |
| 2007/0118151 A1 | 5/2007 | Davidson | |
| 2007/0276437 A1* | 11/2007 | Call | A61B 17/0487 606/232 |
| 2009/0105729 A1 | 4/2009 | Zentgraf | |
| 2011/0060407 A1 | 3/2011 | Ketai et al. | |
| 2011/0301699 A1 | 12/2011 | Saadat | |
| 2012/0130492 A1 | 5/2012 | Eggli et al. | |
| 2013/0096611 A1 | 4/2013 | Sullivan | |
| 2015/0250590 A1 | 9/2015 | Gries et al. | |
| 2017/0245993 A1 | 8/2017 | Gross et al. | |
| 2017/0252032 A1 | 9/2017 | Hiorth et al. | |
| 2018/0185153 A1 | 7/2018 | Bishop et al. | |
| 2018/0250133 A1* | 9/2018 | Reich | A61F 2/2445 |
| 2018/0303614 A1* | 10/2018 | Schaffner | A61F 2/2457 |
| 2019/0343633 A1* | 11/2019 | Garvin | A61B 17/0401 |
| 2020/0297489 A1* | 9/2020 | Bishop | A61B 17/0487 |
| 2020/0337840 A1* | 10/2020 | Reich | A61B 34/10 |
| 2021/0000597 A1 | 1/2021 | Shuey et al. | |
| 2021/0220138 A1* | 7/2021 | Edmiston | A61B 17/0401 |

FOREIGN PATENT DOCUMENTS

| | | |
|---|---|---|
| WO | 2015193728 A2 | 12/2015 |
| WO | 2020109599 A1 | 6/2020 |
| WO | 2020123719 A1 | 6/2020 |

OTHER PUBLICATIONS

"Fish Fighter® Kwik-Pull™ Anchor Retriever" Fish Fighter Products, 6 pages, URL: https://fishfighterproducts.com/shop/fish-fighter-kwik-pull-anchor-retriever/ Retrieved Aug. 29, 2020.

"Knotless SutureTak® Anchor" Arthrex, 2 pages, 1 page, URL: https://www.arthrex.com/resources/animation/2d7_OmxWw0edpgFLMMbz5A/knotless-suturetak-anchor. Retrieved Aug. 29, 2020.

"Shoulder Labral Repair with Knotless SutureTak® Anchor" Arthrex, retrieved Aug. 29, 2020, URL: https://www.arthrex.com/resources/animation/9cpCPTZLCEGvYQFMdlKwxg/shoulder-labral-repair-with-knotless-suturetak-anchor 7 pages. Retrieved Aug. 29, 2020.

"Knotless SutureTak Anchor Instability Repair" Arthrex, 6 pages, 2018.

APS—Annapolis Performance Sailing., "Ronstan Constrictor Rope Clutch| Expert Review"—YouTube, 3 pages. Retrieved Oct. 9, 2020.

International Search Report and Written Opinion for the International Patent Application No. PCT/US2021/051722, mailed Jan. 7, 2022, 10 pages.

* cited by examiner

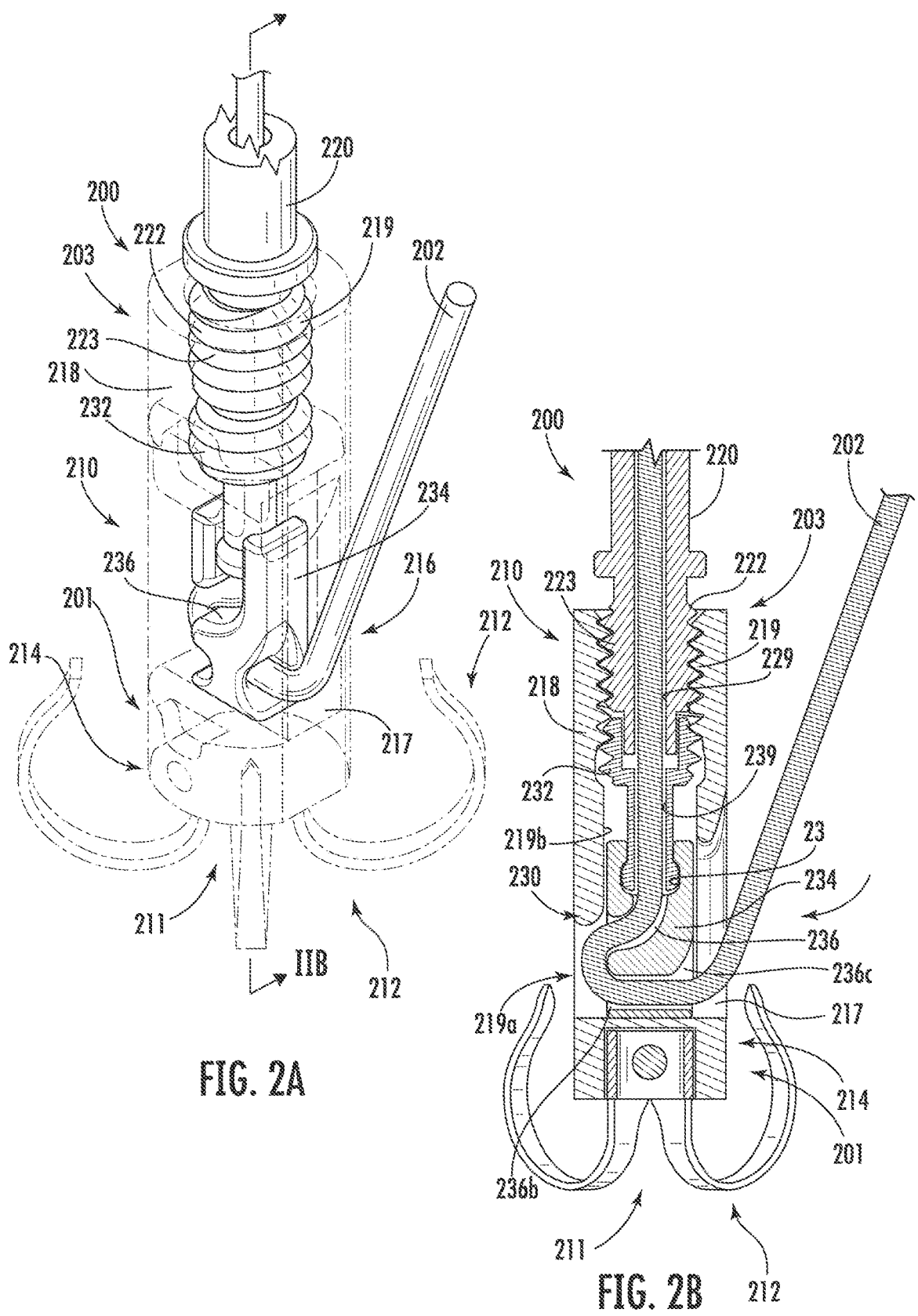

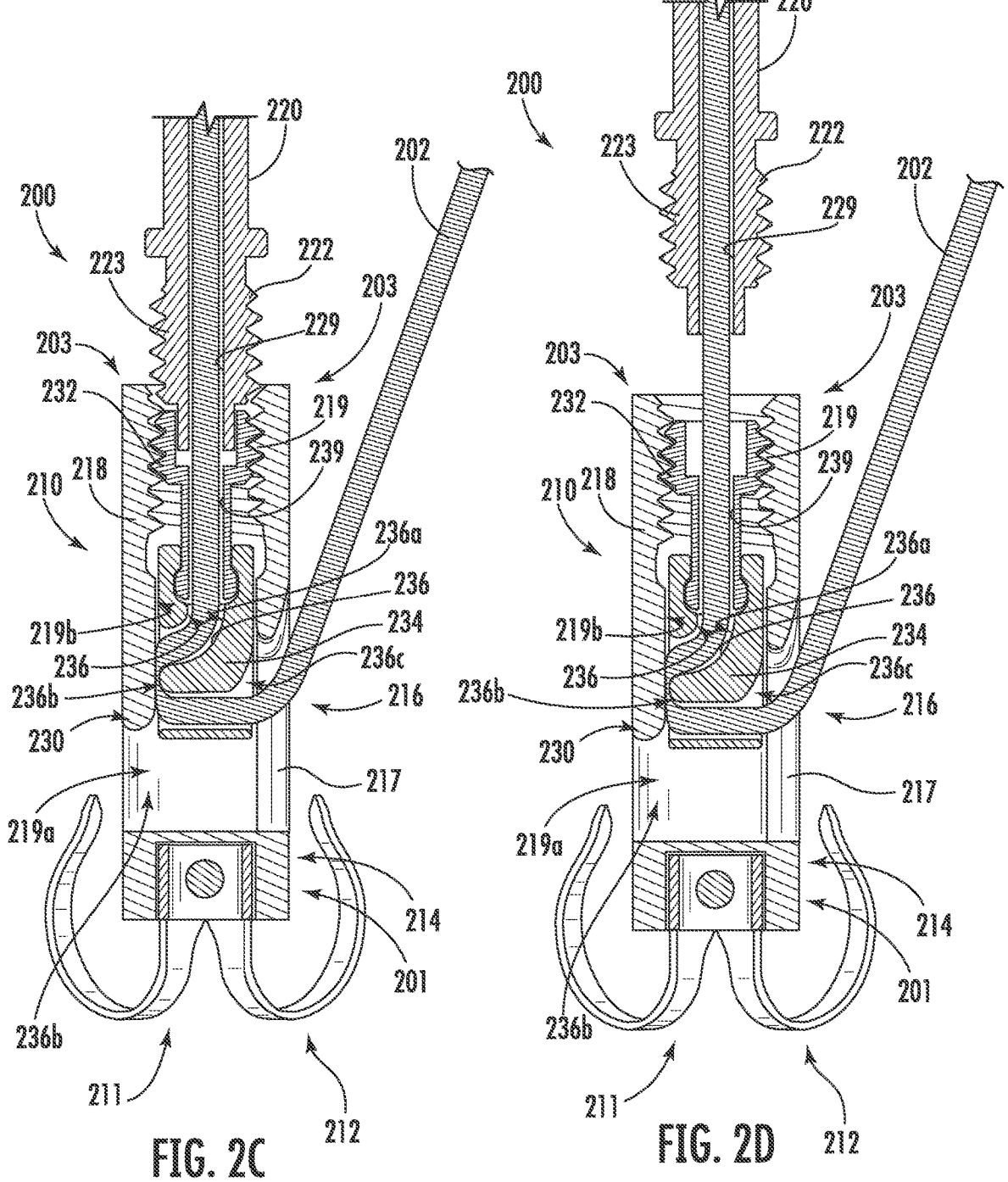

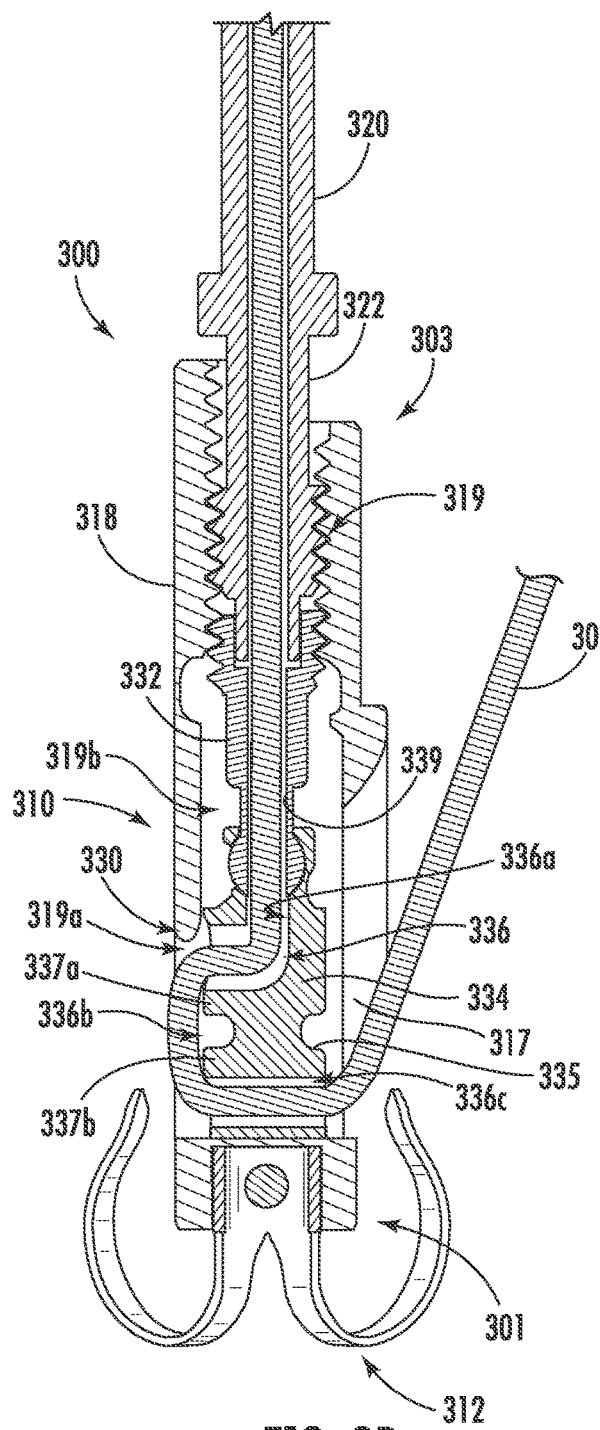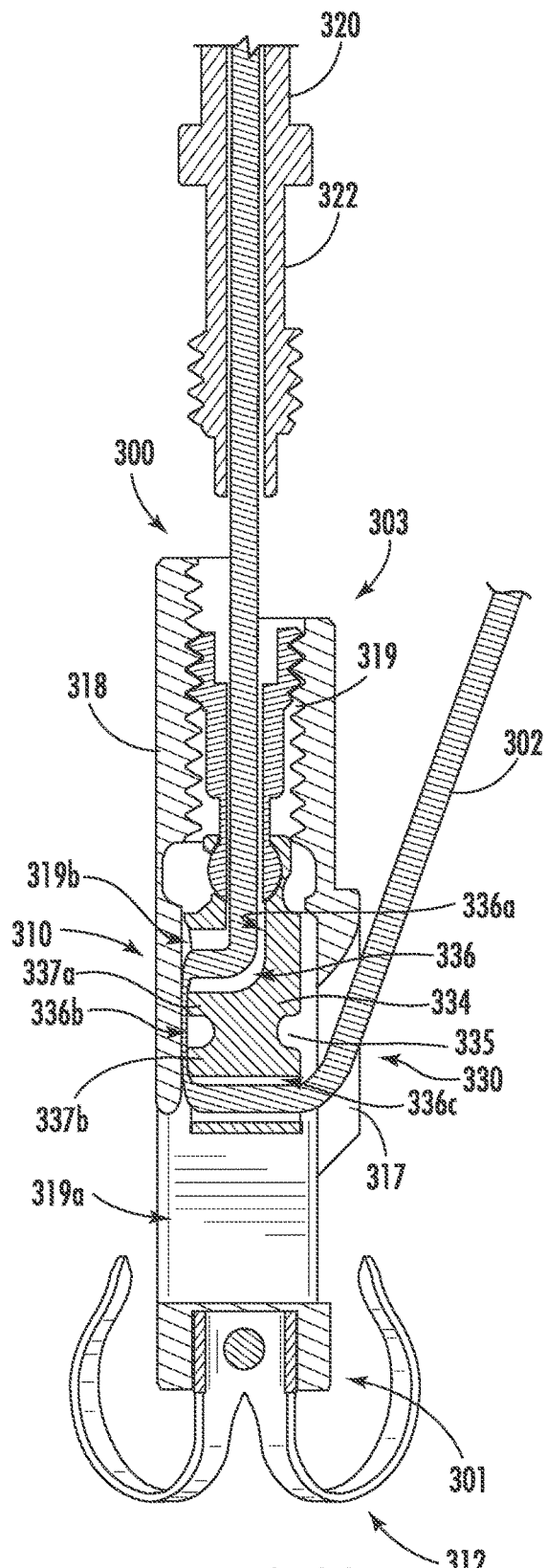
FIG. 3B
FIG. 3C

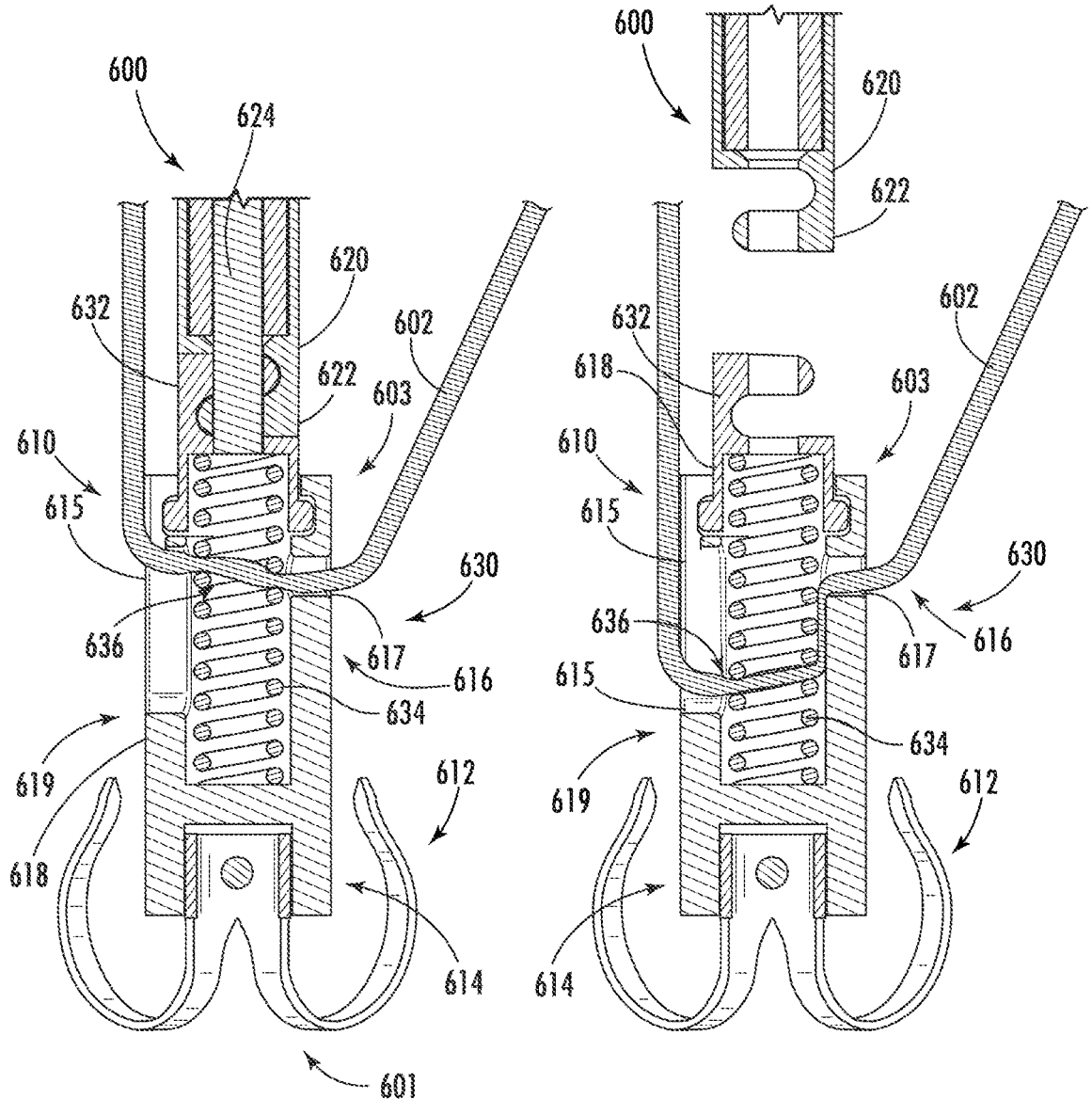

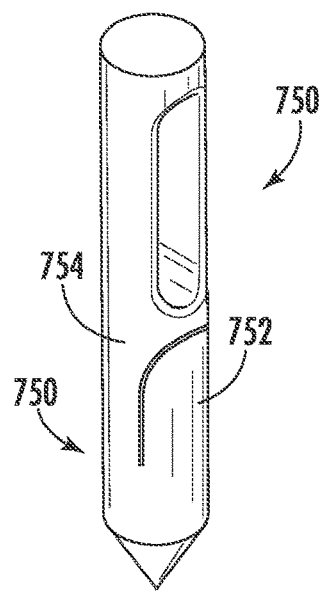
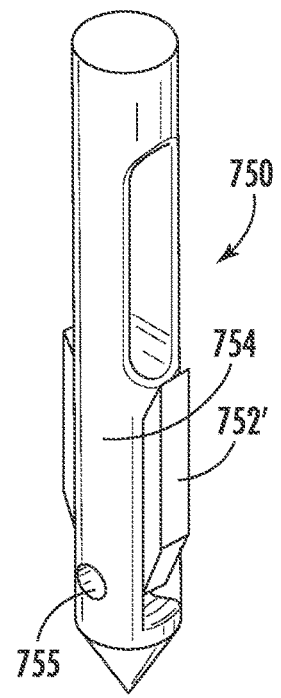
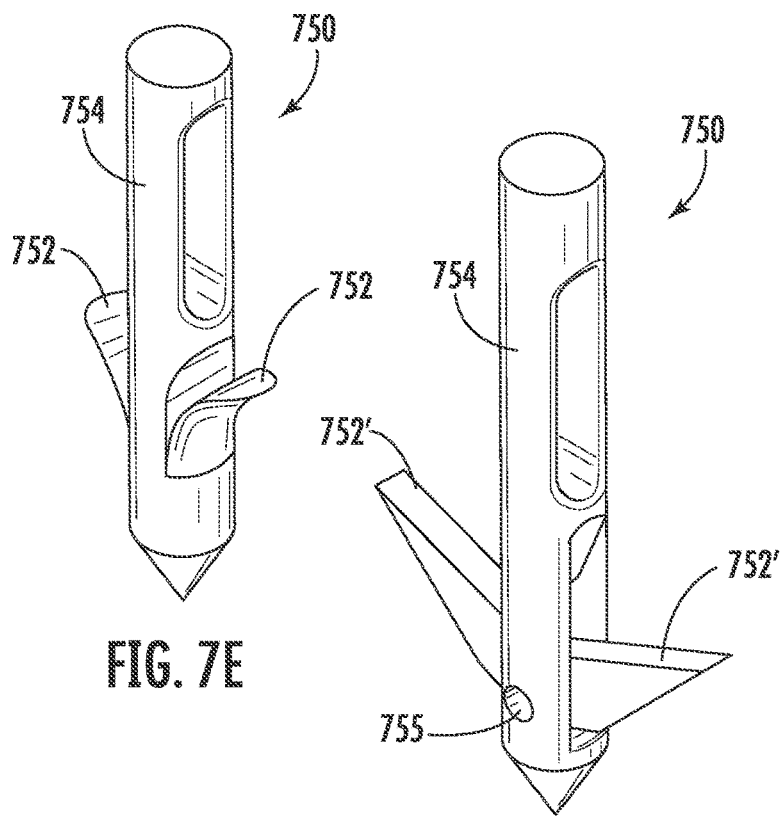
FIG. 7D
FIG. 7F
FIG. 7E
FIG. 7G

DEVICES, SYSTEMS, AND METHODS FOR ADJUSTABLY TENSIONING ARTIFICIAL CHORDAE TENDINEAE IN A HEART

PRIORITY

The present application is a non-provisional of, and claims the benefit of priority under 35 U.S.C. § 119 to, U.S. Provisional Application Ser. No. 63/085,390, filed Sep. 30, 2020, the disclosure of which is hereby incorporated herein by reference in its entirety for all purposes.

FIELD

The present disclosure relates generally to medical devices, systems, and methods for repairing a heart. More particularly, the present disclosure relates to medical devices, systems, and methods for delivering and implanting artificial chordae tendineae in a heart. Even more particularly, the present disclosure relates to medical devices, systems, and methods for adjusting tension of artificial chordae tendineae in a heart.

BACKGROUND

Heart disease, including atrioventricular heart valve malfunctions, impedes patient cardiac output, which reduces patient quality of life and lifespan. The proper flow of blood through the heart is regulated, inter alia, by heart valves, including atrioventricular heart valves, which include soft tissue leaflets which cyclically open and close to allow blood to flow through in one direction. Healthy leaflets prevent blood flow in the opposite direction (regurgitation). Chordae tendineae, extending from the leaflets to the papillary muscles, support the proper functioning of the leaflets, such as by distributing load to the papillary muscles during systolic closure, and by preventing the leaflet from flailing into the atrium. Improper functioning of the chordae tendineae compromises the capacity of the leaflets to form a seal at the heart valve. Various defects of failure of the chordae tendineae, such as elongation, rupture, thickening, retraction, calcification, inelastic stretching or other changes in elasticity, etc., may result in improper closure of the heart valve and/or a flailing leaflet that may no longer have the capacity to form a valving seal for normal heart function.

There is a need for minimally invasive solutions to repair a heart valve, such as the leaflets thereof, while maintaining the option for future interventions. Moreover, there is need for improvements to devices, systems, and methods for repositioning, repairing, and/or replacing one or more chordae tendinea of a heart to improve treatments of heart disease.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In one aspect, the present subject matter is directed to the field of medical devices, systems, and methods for delivering artificial chordae tendineae in a patient and adjusting tension on the artificial chordae tendineae.

In various embodiments described or otherwise within the scope of the present disclosure, a system for adjusting tension in an artificial chordae tendineae extending between a leaflet of a heart valve and papillary muscle or a heart wall includes: an artificial chordae tendineae; a leaflet clip configured to be engaged with a leaflet of a heart valve and with the artificial chordae tendineae; an anchor configured to be engaged with a papillary muscle or heart wall; and a locking assembly associated with the anchor. In various embodiments, the locking assembly is configured to be selectively shiftable between a tension-adjusting configuration allowing the artificial chordae tendineae to move relative to the locking assembly to increase or decrease tension on the leaflet, and a tension-setting configuration inhibiting movement of the artificial chordae tendineae relative to the locking assembly to set tension on the leaflet.

In some embodiments, the locking assembly includes a housing and a movable locking element movable within a longitudinal cavity defined in the housing to shift the locking assembly between the tension-adjusting configuration and the tension-setting configuration. In some embodiments, the movable locking element includes one of a carriage, a roller, an auger, or a tissue-engaging element movable axially within the longitudinal cavity in the housing. In some embodiments, a pathway is defined along the movable locking element along which the artificial chordae tendineae extends. In some embodiments, the longitudinal cavity in the housing defines a locking region and a tension-adjusting region; the artificial chordae tendineae is movable with respect to the movable locking element when the movable locking element is within the tension-adjusting region; a portion of the pathway extends along an exterior of the movable locking element; and a portion of the artificial chordae tendineae extending along the portion of the pathway extending along an exterior of the movable locking element is pinched between the movable locking element and the tension-adjusting region when the movable locking element is within the locking region to set tension on the leaflet. In some embodiments, the system further includes a stylet engageable with the movable locking element to move the movable locking element to shift the locking assembly between the tension-adjusting configuration and the tension-setting configuration. In some embodiments, the system further including a coupler configured to couple the stylet and the movable locking element, where the artificial chordae tendineae extends axially through the stylet, the coupler, and the movable locking element, and transversely through the movable locking element to the portion of the pathway extending along an exterior of the movable locking element, and transversely through the housing to the leaflet clip.

In some embodiments, the system further includes a stylet engageable with the movable locking element to move the movable locking element to shift the locking assembly between the tension-adjusting configuration and the tension-setting configuration.

In some embodiments, the anchor includes a body portion, a tissue-engaging portion extending distally from the tissue engaging portion, and a locking portion extending proximally from the body portion; and the housing is a portion of the locking portion of the anchor.

In various embodiments described or otherwise within the scope of the present disclosure, a device for adjusting tension in an artificial chordae tendineae includes: an artificial chordae tendineae; a housing defining a longitudinal cavity therein; a locking assembly positioned in the housing and having a movable locking element axially movable within the longitudinal cavity of the housing between a tension-adjusting configuration allowing the artificial chordae tendineae to move relative to the housing, and a tension-setting configuration inhibiting movement of the artificial chordae tendineae relative to the housing; and a coupler extending from the movable locking element and configured for engagement with an actuator for moving the movable locking element with respect to the housing.

In some embodiments, the device further includes a tissue-engaging element configured to engage tissue of a heart to anchor an end of the artificial chordae tendineae with respect to the heart.

In some embodiments, the movable locking element includes one of a carriage, a roller, an auger, or a tissue-engaging element. In some embodiments, a pathway is defined along the movable locking element along which the artificial chordae tendineae extends. In some embodiments, a portion of the pathway extends transversely through the movable locking element. Alternatively, or additionally, in some embodiments a portion of the pathway extends along an exterior of the movable locking element. In some embodiments, the longitudinal cavity in the housing defines a locking region and a tension-adjusting region; the artificial chordae tendineae is movable with respect to the movable locking element when the movable locking element is within the tension-adjusting region; and a portion of the artificial chordae tendineae extending along the portion of the pathway extending along an exterior of the movable locking element is pinched between the movable locking element and the tension-adjusting region when the movable locking element is within the locking region to set tension on the leaflet.

In accordance with various principles of the present disclosure, a method of adjusting tension in an artificial chordae tendineae extending between a leaflet of a heart valve and papillary muscle or a heart wall is also disclosed. The method includes: extending an artificial chordae tendineae through a locking assembly of an artificial chordae tendineae tensioning and locking device; moving the artificial chordae tendineae relative to the housing to increase or decrease tension on the leaflet when the locking assembly is in the tension-adjusting configuration; and, when a desired tension on the leaflet is reached, shifting the locking assembly into the tension-setting configuration to set tension on the artificial chordae tendineae and on the leaflet.

In one aspect, moving the artificial chordae tendineae relative to the housing further includes coupling a stylet with the movable locking element of the locking assembly to move the movable locking element. In some embodiments, the locking assembly includes a movable locking element, the method further including associating the artificial chordae tendineae with the movable locking element so that the artificial chordae tendineae is inhibited from moving relative to the housing when the locking assembly is in the tension-setting configuration.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 2A is a perspective view of an artificial chordae tendineae tensioning and locking device formed in accordance with principles of the present disclosure with a housing portion thereof in phantom.

FIG. 2B is a cross-sectional view along line IIB-IIB of an artificial chordae tendineae tensioning and locking device as in FIG. 2A with a housing portion in phantom, and shown in an unlocked configuration.

FIG. 2C is a cross-sectional view of an artificial chordae tendineae tensioning and locking device similar to that of FIG. 2B, but shown in a locked configuration.

FIG. 2D is a cross-sectional view similar to that of FIG. 2C, showing an actuator formed in accordance with principles of the present disclosure disengaged from the artificial chordae tendineae tensioning and locking device.

FIG. 3B is a cross-sectional view along line IIIB-IIIB of an artificial chordae tendineae tensioning and locking device as in FIG. 3A with a housing portion in phantom, and shown in an unlocked configuration.

FIG. 3C is a cross-sectional view of an artificial chordae tendineae tensioning and locking device similar to that of FIG. 3B, but shown in a locked configuration.

FIG. 6B is a cross-sectional view along line VIB-VIB of an artificial chordae tendineae tensioning and locking device as in FIG. 6A with a housing portion in phantom, and shown in an unlocked configuration.

FIG. 6C is a cross-sectional view of an artificial chordae tendineae tensioning and locking device similar to that of FIG. 6B, but shown in a locked configuration.

FIG. 7D is an elevational view of an alternative embodiment of an anchor portion, shown in an insertion configuration, usable in an artificial chordae tendineae tensioning and locking device as in FIG. 7A.

FIG. 7E is an elevational view of the anchor portion of FIG. 7D shown in an anchoring configuration.

FIG. 7F is an elevational view of an alternative embodiment of an anchor portion, shown in an insertion configuration, usable in an artificial chordae tendineae tensioning and locking device as in FIG. 7A.

FIG. 7G is an elevational view of the anchor portion of FIG. 7F shown in an anchoring configuration.

DETAILED DESCRIPTION

Figure 1:
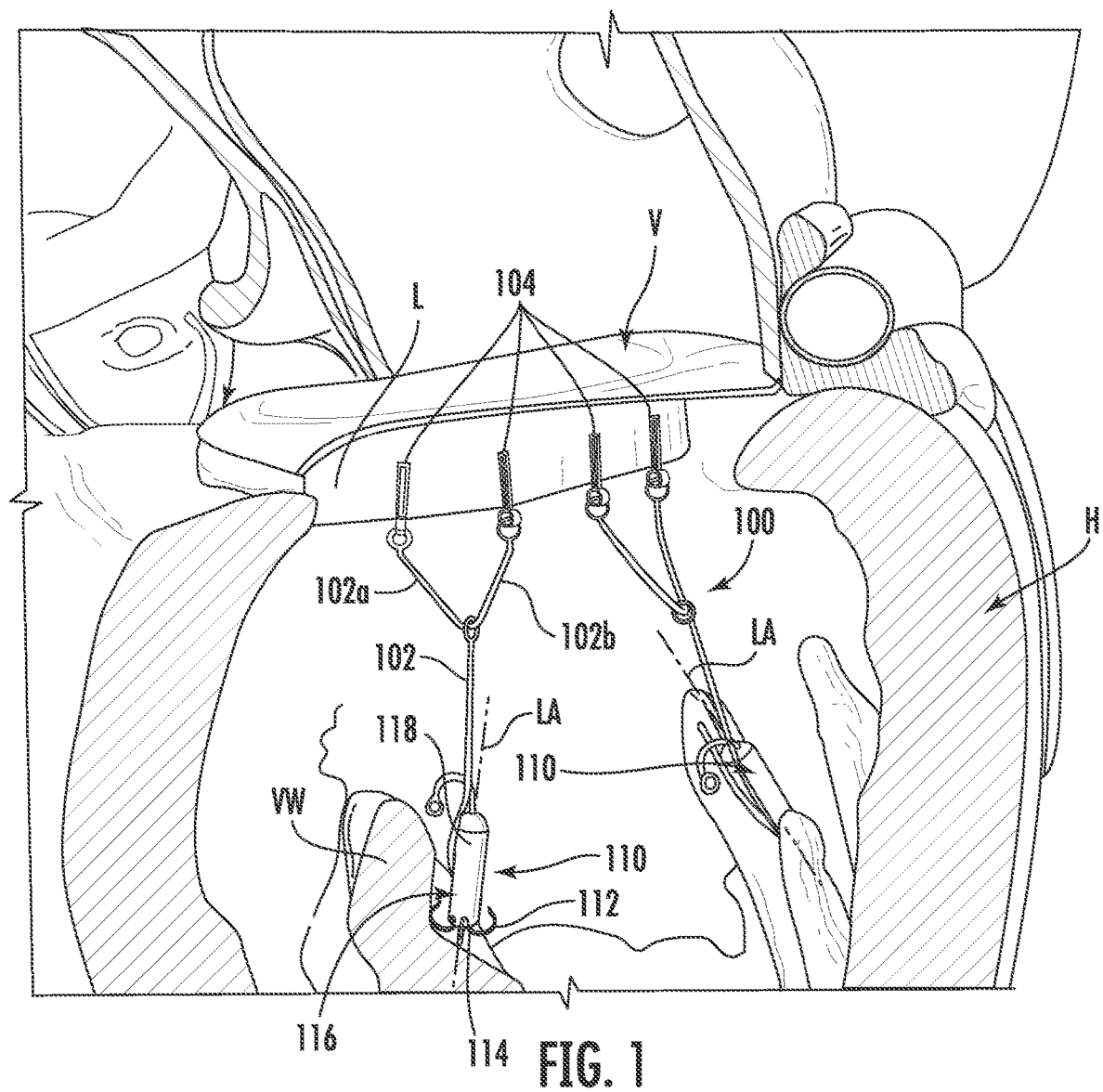
FIG. 1 is a schematic cross-sectional view of a human heart with an example of a heart valve repair device shown being implanted to repair a mitral valve annulus with an artificial chordae tendineae tensioning and locking device formed in accordance with aspects of the present disclosure.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, a cavity, or a bore.

In accordance with various principles and aspects of the present disclosure, one or more leaflets of a heart valve are repositioned and/or repaired by implanting artificial chordae tendineae in the heart extending between the leaflet and the ventricular wall and/or papillary muscle. Various embodiments of devices and systems including a device for adjusting and/or setting tension in the artificial chordae tendineae are disclosed herein, and/or methods (such as a minimally invasive method) of using such devices and/or systems to implant and/or to adjust the tension of and/or to set the tension of the artificial chordae tendineae are disclosed herein for use in repairing a heart valve. An example of an artificial chordae tendineae tensioning and locking system 100 is illustrated in FIG. 1 with reference to a mitral valve. It will be appreciated that the artificial chordae tendineae tensioning and locking system 100 may be used in other contexts, such as repair of a tricuspid valve One end of the artificial chordae tendineae 102 is attached (e.g., via a leaflet clip 104, such as a spring clip) to a free edge of the leaflet L to be repaired, and the other end of the artificial chordae tendineae 102 is connected (e.g., via an anchor 110, such as a ventricle anchor) to the heart H (e.g., the ventricle wall or papillary muscle VW). The artificial chordae tendineae 102 (e.g., length and/or tension thereof) is adjusted to adjust the relative positions of the leaflet clip 104 and the anchor 110 (e.g., to bring the leaflet clip 104 and the anchor 110 closer together or farther apart) to adjust/repair the valve leaflet L, such as to minimize regurgitation of blood through the valve V.

In some embodiments, devices and systems for repairing the heart valve are delivered via a catheter or other appropriate delivery device to the treatment site (e.g., mitral valve or bicuspid valve). The system may have one or more controls disposed at a proximal end thereof to enable a user to manipulate the disclosed devices. As will be appreciated, the specific nature of the delivery device is not critical to the present disclosure as long as the delivery device is configured to allow a user to deliver, implant, and manipulate the disclosed devices at a targeted location within the heart. It will also be appreciated that delivery, engagement, and manipulation of the disclosed devices may be facilitated by use of known visualization techniques, such as fluoroscopy, ultrasound, intracardiac echocardiography (ICE), transesophageal echocardiogram, or the like.

The delivery catheter is advanced to the treatment site in the ventricle. A leaflet clip 104 (such as a spring clip), may be manufactured or otherwise provided on the side of the delivery catheter, such as housed in a leaflet grasping mechanism. Once the catheter has reached the treatment site, the leaflet clip 104 is opened and positioned to catch and be secured to the leaflet L (e.g., the free edge of the leaflet). Medical imaging may be used to confirm the location of the leaflet clip 104 and its quality of purchase onto the leaflet L. If the purchase and/or location is undesired, the leaflet clip 104 may be returned to the open position, and the leaflet grasping steps repeated until the placement of the leaflet clip 104 is satisfactory, and the leaflet clip 104 is then left in place on the leaflet L, as illustrated in FIG. 1.

An artificial chordae tendineae 102, formed from any of a variety of appropriate materials, including, without limitation, suture materials, such as polytetrafluoroethylene (PTFE), or ePTFE (expanded PTFE), extends between the leaflet clip 104 to a ventricle anchor 110, configured to anchor the artificial chordae tendineae 102 to the ventricle wall VW (e.g., papillary muscle). In some embodiments, additional artificial chordae tendineae filaments 102a, 102b, etc. may extend between the artificial chordae tendineae 102 extending from the ventricle anchor 110 and between the leaflet clip 104. To deploy and secure the ventricle anchor 110 to the ventricle wall VW, the distal catheter head is positioned above the valve V in the atrium. The working channel is advanced out of the delivery catheter, and medical imaging may be used to assist in positioning the working channel with respect to the desired ventricle anchor location. A rod or actuator or stylet (such terms being used interchangeably herein without intent to limit) attached to the ventricle anchor may be used to deploy the ventricle anchor into the ventricle heart tissue by pushing the ventricle anchor out of the working channel. Medical imaging may be used to confirm the ventricle anchor location and quality of purchase to the heart tissue. If the purchase and/or location is undesired, the stylet may be used to retract the ventricle anchor into the working channel, and the ventricle anchor deployment steps are repeated until placement of the ventricle anchor is satisfactory, and the ventricle anchor is then left in place, as illustrated in FIG. 1.

A final check, such as using medical imaging, to verify the placement of the ventricle anchor 110 may be performed. When satisfied with the placement of the ventricle anchor 110, the working channel optionally may be retracted into the catheter. It will be appreciated that the working channel may remain coupled to the ventricle anchor 110 during tensioning, if desired. The stylet remains coupled with the ventricle anchor.

In accordance with principles of the present disclosure, the anchor 110 is associated with an artificial chordae tendineae tensioning and locking system 100 formed in accordance various aspects and principles of the present disclosure to adjust tension on the artificial chordae tendineae 102 and/or to set or lock or fix (such terms being used interchangeably herein without intent to limit) the tension on the artificial chordae tendineae 102. In various embodiments, the anchor 110 includes a tissue-engaging portion 112, a body portion 114 (from which the tissue engaging portion 112 extends), and a locking portion 116. The locking portion 116 may extend from, or be formed or coupled with, or otherwise associated with (e.g., separate from and coupled to) the anchor body portion 114. A tensioning and locking device (or at least portions or components thereof), shown in further detail in the various embodiments illustrated in the accompanying drawings and described in further detail below, is positioned within a housing 118 which may be associated with (e.g., a portion of, or separate and coupled to) the locking portion 116 of the anchor 110, and couplable with the artificial chordae tendineae 102.

The tensioning and locking device has a tension-adjusting configuration allowing movement of the artificial chordae tendineae 102 relative to the tensioning and locking device (such as to adjust tension of the artificial chordae tendineae 102 on the leaflet). Adjustment of the tension on the artificial chordae tendineae 102 includes paying out or releasing or feeding additional length of artificial chordae tendineae 102 (e.g., moving the artificial chordae tendineae 102 distally) to reduce tension on or in or of the artificial chordae tendineae 102, or pulling on or retracting the artificial chordae tendineae 102 (e.g., moving the artificial chordae tendineae 102 proximally) to increase tension on or in or of the artificial chordae tendineae 102. The tensioning and locking device also has a tension-setting or locking (such terms being used interchangeably herein without intent to limit) configuration inhibiting or preventing or locking movement of the artificial chordae tendineae 102 relative to the tensioning and locking device (such as to set or fix or limit the tension of the artificial chordae tendineae 102 on the leaflet). The tensioning and locking device is selectively shiftable or movable alternately (in either direction) between the tension-adjusting configuration and the locking configuration. An actuator (shown and described in further detail in conjunction with the various embodiments of tensioning and locking devices illustrated in the accompanying drawings and described in further detail below) may be coupled to or engaged with a component of the tensioning and locking device to selectively shift or move the tensioning and locking device between the tension-adjusting configuration and the locking configuration to enable selective movement and/or tensioning of the artificial chordae tendineae 102.

In some embodiments, the artificial chordae tendineae 102 runs continuously from the proximal end of the catheter, through or along the catheter, into and through the tensioning and locking device (and, optionally, through the anchor 110 as well) and to the leaflet L, wherein the artificial chordae tendineae 102 is anchored to the leaflet L, such as with a leaflet clip 104. The artificial chordae 102 may be tensioned from the proximal end of the catheter to decrease the distance between the leaflet clip 104 and the anchor 110 to repair the functioning of the leaflet L. In some embodiments the artificial chordae tendineae 102 can be tensioned from a location adjacent to the proximal end of the delivery system. Such tensioning may be performed to decrease the distance between the leaflet clip 104 and the anchor 110. If it is desired to reduce tension, the artificial chordae tendineae 102 is selectively released to increase the length of artificial chordae tendineae 102 to increase the distance between the leaflet clip 104 and the anchor 110 and thereby reduce tension therebetween. The tensioning and locking device allows the artificial chordae tendineae 102 to be locked and released to adjust the desired tension, such as to increase or to reduce the amount of tension on or in the artificial chordae tendineae 102.

A locking stylet or actuator (such terms being used interchangeably herein without intent to limit) may be provided, running from a proximal catheter handle to the ventricle anchor. A coupling feature may be provided at the distal end of the stylet or actuator to engage the tensioning and locking device. Manipulation of the locking stylet allows the operator to manipulate (e.g., lock or unlock) the tensioning and locking device such as to lock or unlock the artificial chordae tendineae 102 to adjust the tension on the artificial chordae tendineae 102, such as while applying tension or no tension on the artificial chordae tendineae 102. The stylet may be formed of metal or a polymeric material (e.g., a relatively rigid polymer such as PEBAX®). Optionally, a wire may be added to provide additional feedback to the user with regard to the effect of manipulating (e.g., rotating) the stylet. The effect of the artificial chordae tendineae 102 tensioning on the leaflet and valve function may be observed under medical imaging, and further tensioning or loosening by manipulating the locking stylet and artificial chordae may be performed until the desired leaflet repair is achieved. If the artificial chordae tendineae is over-tensioned, as may be evidenced by a visualized regurgitation characteristic of the affected heart valve, the tensioning and locking device can be released and the distance between the leaflet clip 104 and the anchor 110 can be increased by increasing the length of the artificial chordae tendineae 102 therebetween to reduce tension in the artificial chordae tendineae 102. The tension adjustment steps can be repeated as needed or indicated. When satisfied with the artificial chordae tendineae 102 tensioning and valve repair, the artificial chordae tendineae 102 is then detached from the catheter and the catheter is removed from the heart. The procedure can then be concluded or additional artificial chordae tendineae 102 can be implanted. In some embodiments, one or more artificial chordae tendineae 102 may be coupled to one or more leaflet clips 104. When the procedure is complete, the locking stylet or actuator is detached from the tensioning and locking device. The action of retracting the locking stylet from the tensioning and locking device can cut the artificial chordae tendineae proximal of the tensioning and locking device. Alternatively, the locking stylet may be detached from the anchor and removed from the body with the entire catheter. The artificial chordae tendineae may then be strung down a new catheter capable of cutting the artificial chordae tendineae. An artificial-chordae-tendineae-cutting catheter may then be positioned to cut the artificial chordae tendineae, e.g., proximal to the tensioning and locking device. The excess artificial chordae tendineae and artificial chordae tendineae cutting catheter is then removed from the body. Alternatively, a pre-cut artificial chordae tendineae (e.g., of a selected/predetermined length) may be used so that cutting after placement is not necessary, and the proximal end of the pre-cut artificial chordae tendineae is simply left in place (e.g., leaving a tail behind) after the procedure is concluded. The procedure can be concluded or additional artificial chordae tendineae can be implanted.

Various embodiments of artificial chordae tendineae tensioning and locking devices embodying various aspects of the present disclosure and formed in accordance with various principles of the present disclosure are illustrated in the accompanying drawings. For the sake of simplicity, reference will be made herein to simply a tensioning and locking device rather than an artificial chordae tendineae tensioning and locking device. Each of the tensioning and locking devices disclosed herein includes a locking assembly having a tensioning and locking element configured to affect the tension of an artificial chordae tendineae. The locking assembly shifts or moves between a tension-adjusting configuration in which the artificial chordae tendineae is substantially free to move with respect to other components of the locking assembly (such as to adjust tension of the artificial chordae tendineae), and a tension-setting or locking configuration in which movement of the artificial chordae tendineae with respect to other components of the locking assembly (such as to adjust tension of the artificial chordae tendineae) is restricted or inhibited or prevented or locked (such terms being used interchangeably herein without intent to limit). In some embodiments, the tensioning and locking element includes a movable locking element with which the artificial chordae tendineae is associated to adjust the tension of the artificial chordae tendineae. The movable locking element is selectively movable to shift the locking assembly between the locked configuration and the tension-adjusting configuration. In some embodiments, the movable locking element moves along the longitudinal axis LA of the housing in which the tensioning and locking device is positioned. In some embodiments, the locking element is shaped and configured to engage or interact with the artificial chordae tendineae to affect movement of the artificial chordae tendineae relative to other components of the locking assembly.

The tensioning and locking device may be associated, such as coupled to or formed in conjunction with (e.g., sharing housing components of), the anchor 110. In embodiments in which the tensioning and locking device is associated with the anchor 110, a locking portion 116 of the anchor 110 may extend from or be coupled or coextensive with (e.g., as an extension of) the anchor body portion 114. The tensioning and locking device, or at least components thereof, such as a locking assembly thereof, may be housed in a housing 118, such as of the locking portion 116. It will be appreciated that the housing 118 may, in some embodiments, be separate from or extend from or otherwise be associated with the locking portion 116.

The tensioning and locking devices of the disclosed embodiments are configured to allow adjustment and/or locking (e.g., setting or fixing) of tension on or of or in (such terms being used interchangeably herein without intent to limit) an artificial chordae tendineae, such as to apply a desired amount of tension, such as between a valve leaflet and papillary muscle/heart wall. In some embodiments, the artificial chordae tendineae 102 may enter the housing 118 via the delivery catheter and via the actuator, substantially along the longitudinal axis LA of the housing 118, and exit from a side of the housing 118. In some embodiments, other components extend through the delivery catheter, and the artificial chordae tendineae 102 extends, instead, along (e.g., outside, an optionally in an overtube) the delivery catheter and enters the housing 118 through a side of the housing 118. In various of the disclosed embodiments, the tensioning and locking device allows reversible locking and unlocking to allow tension to be set and released to allow the tension to be readjusted if needed or desired, such as through the use of a control element or actuator. Tensioning and locking may be adjusted while the heart is actively beating. It will be appreciated that various features of one embodiment may be used in conjunction with or instead of features of another embodiment. Accordingly, the features described herein are illustrated in various combinations as examples of manners in which such features may be combined and embodied into an artificial chordae tendineae tensioning and locking device providing the various benefits disclosed herein.

Turning now to the drawings, an example of an embodiment of a tensioning and locking device 200 formed in accordance with principles of the present disclosure is illustrated in FIG. 2A as associated with an anchor 210 (although other configurations are within the scope of the present disclosure). The anchor 210 includes a tissue engaging portion 212 (configured to engage and/or anchor into tissue, such as heart tissue), at a distal end 211 of the anchor 210, extending distally from a body portion 214 of the anchor 210. A locking portion 216 extends proximally from the body portion 214 of the anchor 210. A locking assembly 230 of the tensioning and locking device 200 may be housed in a housing 218, which in some embodiments is associated with the locking portion 216 of the anchor 210, as illustrated in FIGS. 2B, 2C, and 2D and discussed in further detail below. The artificial chordae tendineae 202 extends into the proximal end 203 of the tensioning and locking device 200 to be engaged with or to interact with (such terms being used interchangeably herein without intent to limit) the tensioning and locking device components of the locking assembly 230 within the housing 218 (to allow adjustment and/or setting of tension on the artificial chordae tendineae 202), and extends out an exit opening or aperture or window 217 in the housing 218 to extend to a heart leaflet at which a free end of the artificial chordae tendineae 202 may be anchored such as via a leaflet clip, such as described above with reference to FIG. 1. In the illustrated embodiment, the artificial chordae tendineae 202 extends substantially axially along the longitudinal axis LA of the housing 218 and into the housing 218 through a catheter 220 and stylet 222. However, as noted above, other entrance points for the artificial chordae tendineae 202 are within the scope and spirit of the present disclosure. The stylet 222 is engaged with a longitudinal bore or cavity 219 (such terms being used interchangeably herein without intent to limit, the term bore not being limited to a circular cross-sectional shape) in the housing 218 to actuate the locking assembly 230 of the tensioning and locking device 200, as will now be described with reference to FIGS. 2B, 2C, and 2D, in which various components of the tensioning and locking device 200 and the locking assembly 230, and their interactions with the artificial chordae tendineae 202, are illustrated.

In the example of a stylet configuration illustrated in FIG. 2B, the stylet 222 includes a threaded distal end 223 threadedly engaged within a threaded portion of a proximal portion of the longitudinal bore or cavity 219 in the housing 218. The stylet 222 also engages a coupler 232 extending from (and optionally coupled to) a moveable element, such as a carriage 234, of the locking assembly 230 of the tensioning and locking device 200. The coupler 232 may also be threadedly engaged within the longitudinal cavity 219 of the housing 218 to be rotationally advanced distally or retracted proximally by the stylet 222. As such, the stylet 222 and the coupler 232 are engaged to allow rotation of the stylet 222 to be transmitted to the coupler 232 to rotate the coupler 232 within the longitudinal cavity 219. Examples of such engagement include, without limitation, a lock in key configuration, such as a noncircular projection on one of the stylet 222 and the coupler 232 engaged in a corresponding noncircular bore in the other of the stylet 222 and the coupler 232, a slot in one of the stylet 222 and the coupler 232 and a longitudinally extending rib in the other of the stylet 222 and the coupler 232, and other engagements locking against relative rotational movement as known or heretofore known in the art. Also, the coupler 232 is coupled to the carriage 234 to cause axial advancement or retraction of the carriage 234 as the coupler 232 axially advances or retracts, but not to cause relative rotation between the carriage 234 and the housing 218 (for reasons such as will become apparent). Examples of such engagement include, without limitation, engagement of a circumferentially extending rib along a distally-extending portion of the coupler 232 (e.g., extending distally from the threaded portion of the coupler 232) within a circumferentially extending groove within the carriage 234 and receiving the distally-extending portion of the coupler 232, and other engagements locking against relative rotational movement. In the illustrated embodiment, the carriage 234 is positioned within a portion of the longitudinal cavity 219 within the housing 218 distal to the threaded portion of the longitudinal cavity 219. The longitudinal cavity 219 may include a tension-adjusting region 219*a* having a first diameter and locking region 219*b* having a second diameter, the first diameter being larger than the second diameter to allow adjustment of the tension on or in the artificial chordae tendineae 202 (as explained in further detail below). As used herein, the term "diameter" is generally to be understood as the dimension transverse to the longitudinal dimension, such as a width dimension, and is not limited to a dimension of a circular shape or cross-section. The locking region 219*b* may be formed by a narrowing of the diameter of the longitudinal cavity 219 relative to the tension-adjusting region 219*a*, such as by a shoulder or other protrusion extending into and narrowing the diameter of the longitudinal cavity 219 in the locking region 219*b*. In the illustrated embodiment, the tension-adjusting region 219*a* is closer to the distal end 201 of the tensioning and locking device 200 than the proximal end 203 of the tensioning and locking device 200. However, a reverse configuration is within the scope of the present disclosure.

When the tensioning and locking device 200 is delivered (and the anchor 210 deployed or secured to tissue), the carriage 234 is positioned within the tension-adjusting region 219*a*, as illustrated in FIG. 2B. The artificial chordae tendineae 202 extends along a pathway 236, such as formed partially through and partially along the exterior of the carriage 234, to be coupled with the carriage 234, and then exits the housing 218 via the exit 217 in the housing 218. For instance, the artificial chordae tendineae 202 may extend through a longitudinal portion 236*a* of the pathway 236 (e.g., a longitudinal bore extending axially within the carriage 234) to enter into engagement with the carriage 234 (such as upon exiting a longitudinal cavity 229 through the stylet 222 and a longitudinal cavity 239 through the coupler 232), along a peripheral portion 236*b* (e.g., along the exterior of the carriage 234), and through a transverse portion 236*c* (such as extending transversely through the carriage 234 so that the artificial chordae tendineae 202 moves axially with the carriage 234, along the longitudinal axis LA of the housing 218, upon axial translation of the carriage 234 along the longitudinal cavity 219 within the housing 218). When the carriage 234 is in the tension-adjusting region 219*a*, the artificial chordae tendineae 202 is substantially freely movable along the pathway 236 and relative to the carriage 234 and the locking assembly 230 and the anchor 210 to allow adjustment of the tension in or on or of the artificial chordae tendineae 202. Tension on the artificial chordae tendineae 202 may be adjusted by pulling on the artificial chordae tendineae 202 proximally (such as to increase tension) or feeding or paying out or otherwise releasing or feeding (such terms being used interchangeably herein without intent to limit) additional artificial chordae tendineae 202 distally (such as to reduce tension).

Once the desired tension in or on the artificial chordae tendineae 202 has been reached, the tension may be fixed or set or locked (such terms being used interchangeably herein without intent to limit). The stylet 222 is actuated (e.g., rotated), to actuate the coupler 232 to be moved proximally (towards the proximal end 203 of the tensioning and locking device 200), thereby moving the carriage 234 proximally. As illustrated in FIG. 2C, when the carriage 234 is advanced towards the locking region 219b in the longitudinal cavity 219 such that the portion of the artificial chordae tendineae 202 running along the exterior portion of the pathway 236 on the carriage 234 faces the locking region 219b, that portion of the artificial chordae tendineae 202 is caught or held between the carriage 234 and the locking region 219b. The tension on the artificial chordae tendineae 202 may thereby be fixed. If further adjustment of the tension is desired, then the stylet 222 may be actuated (e.g., rotated) to move the carriage 234 distally (towards the distal end 201 of the tensioning and locking device 200) to release the hold of the locking region 219b on the artificial chordae tendineae 202 to allow the tension on the artificial chordae tendineae 202 to be adjusted (e.g., by paying out or releasing or feeding additional length of artificial chordae tendineae 202 to reduce tension thereon, or to pull on or retract the artificial chordae tendineae 202 proximally to increase tension thereon). Upon determining the desired tension on the artificial chordae tendineae 202 has been reached, the stylet 222 may be decoupled from the coupler 232 (such as by continued rotation of the stylet 222 to disengage from the threading within the threaded portion of the longitudinal cavity 219 within the housing 218) and removed. A portion of the artificial chordae tendineae 202 may thus be locked within the locking portion 216 of the housing 218, and the artificial chordae tendineae 202 proximally extending from the housing 218 may be cut, and the artificial chordae tendineae 202 left in place anchored between the heart tissue and the leaflet to function as a chordae tendineae.

In the embodiment of FIGS. 2A-2D, the carriage 234 may have a substantially rectangular cross-section. An alternative configuration of a locking assembly similar to the locking assembly 230 of FIGS. 2A-2D, but having a carriage with a substantially round cross-section, is shown in connection with the tensioning and locking device 300 illustrated in FIGS. 3A-3C. The carriage 334 of the locking assembly 330 functions substantially the same as or similar to the carriage 234 of the locking assembly 230 shown in and described with reference to FIGS. 2A-2D, with some additional features or benefits. It will be appreciated that other than some differences between the carriages 234, 334, the tensioning and locking devices 200 and 300 of FIGS. 2A-2D and FIGS. 3A-3C, respectively, can be arranged and operate in substantially the same or similar manners. For example, the tensioning and locking device 300 is illustrated as associated with an anchor 310 having a tissue-engaging portion 312, a body portion 314, and a locking portion 316). For the sake of brevity and convenience, and without intent to limit, similar elements with similar functions are indicated with the same reference characters differing in value by 100, reference being made to the above descriptions of those similar elements and functions and operations thereof.

Figure 3A:
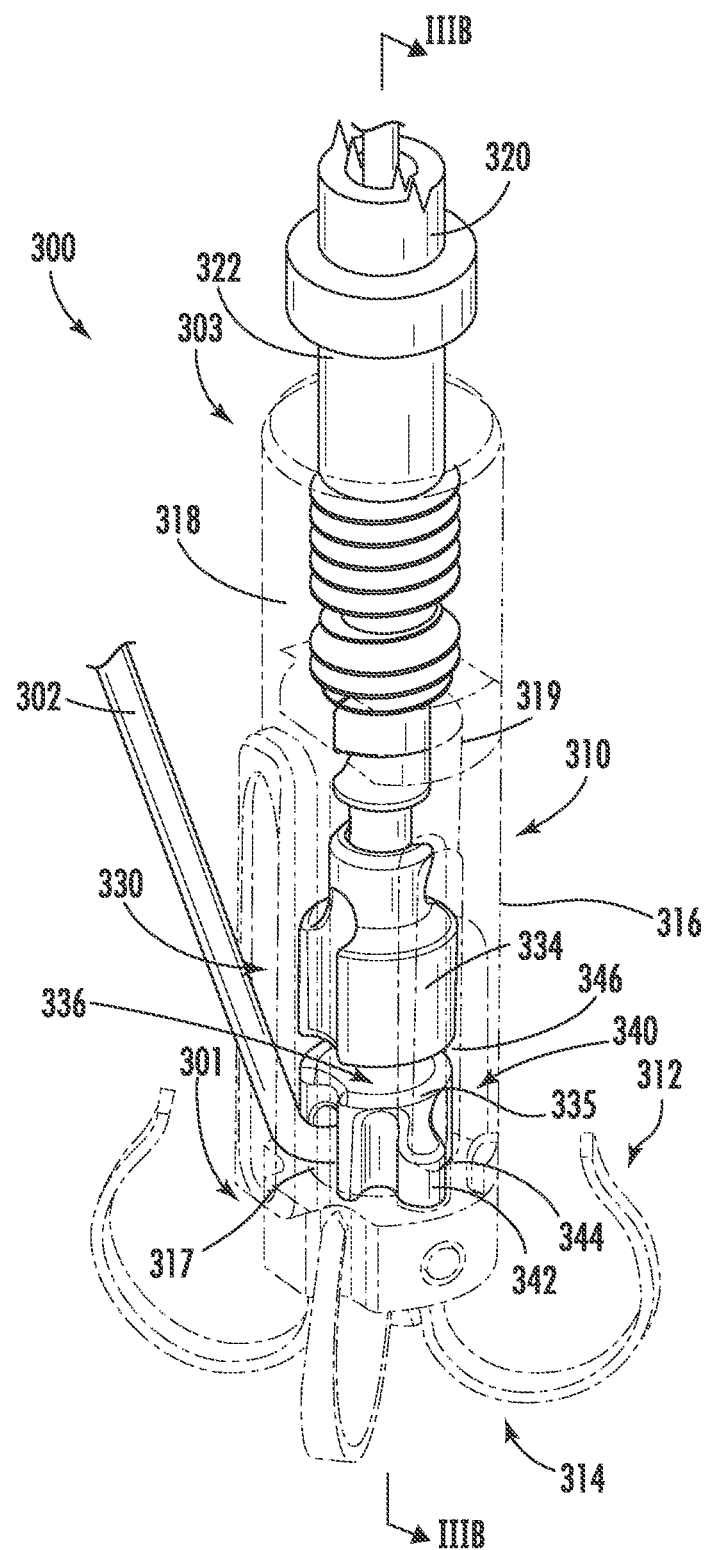
FIG. 3A is a perspective view of an artificial chordae tendineae tensioning and locking device formed in accordance with principles of the present disclosure with a housing portion in phantom.

Like the artificial chordae tendineae 202 of FIGS. 2A-2C, the artificial chordae tendineae 302 illustrated in FIGS. 3A-3C may extend through a stylet 322 and catheter 320 and into a proximal end 303 of the locking device 300 and through a longitudinal cavity 339 through a coupler 332 to enter into engagement with the carriage 334. Also like the artificial chordae tendineae 202 and carriage 234 illustrated in FIGS. 2A-2D, the artificial chordae tendineae 302 illustrated in FIGS. 3A-3C extends along a pathway 336 formed partially along and partially transversely through the exterior of the carriage 334 so that the artificial chordae tendineae 302 is caused to move axially along the longitudinal axis LA of the housing 318 upon axial translation of the carriage 334 along the longitudinal cavity 319 within the housing 318. However, in contrast with the carriage 234 shown in the locking assembly 230 illustrated in FIGS. 2A-2D, the carriage 334 of the locking assembly 330 illustrated in FIGS. 3A-3C has a circumferential groove 335 between the exit point from the longitudinal portion 336a of the pathway 336 (e.g., a longitudinal bore within the carriage 334) to the exterior portion 336b of the pathway 336, and the entrance point from the exterior portion 336b of the pathway 336 into the transverse portion 336c of the pathway 336 through the carriage 334). The circumferential groove 335 may provide or define two pinch points 337a, 337b at which the artificial chordae tendineae 302 can be pinched between the carriage 334 and the locking region 319b of the longitudinal cavity 319 in the housing 318. As the carriage 334 moves from the tension-adjusting region 319a (in which relatively unrestricted movement of the artificial chordae tendineae 302 within the pathway 336 allows adjustment of tension of the artificial chordae tendineae 302) to the locking region 319b (e.g., towards the distal end 301 of the tensioning and locking device 300 in the illustrated example), the artificial chordae tendineae 302 becomes pinched between the pinch points 337a, 337b and the inner wall of the longitudinal cavity 319, thereby fixing the tension in the artificial chordae tendineae 302.

In some embodiments, a clock feature 340 may be provided to inhibit rotation of the carriage 334 within the longitudinal cavity 319, such as to guide the path of the artificial chordae tendineae 302 through the housing 318 (e.g., by positioning the pathway 336 for the artificial chordae tendineae 302 along or around the carriage 334 with the exit 317 in the housing 318). For instance, a detent or rib or protrusion 342 (such terms being used interchangeably herein without intent to limit) may be provided in the carriage 334 engaging a corresponding groove 344 and/or window 346 in the housing 318. It will be appreciated that other configurations are within the scope of the present disclosure.

Figure 4A:
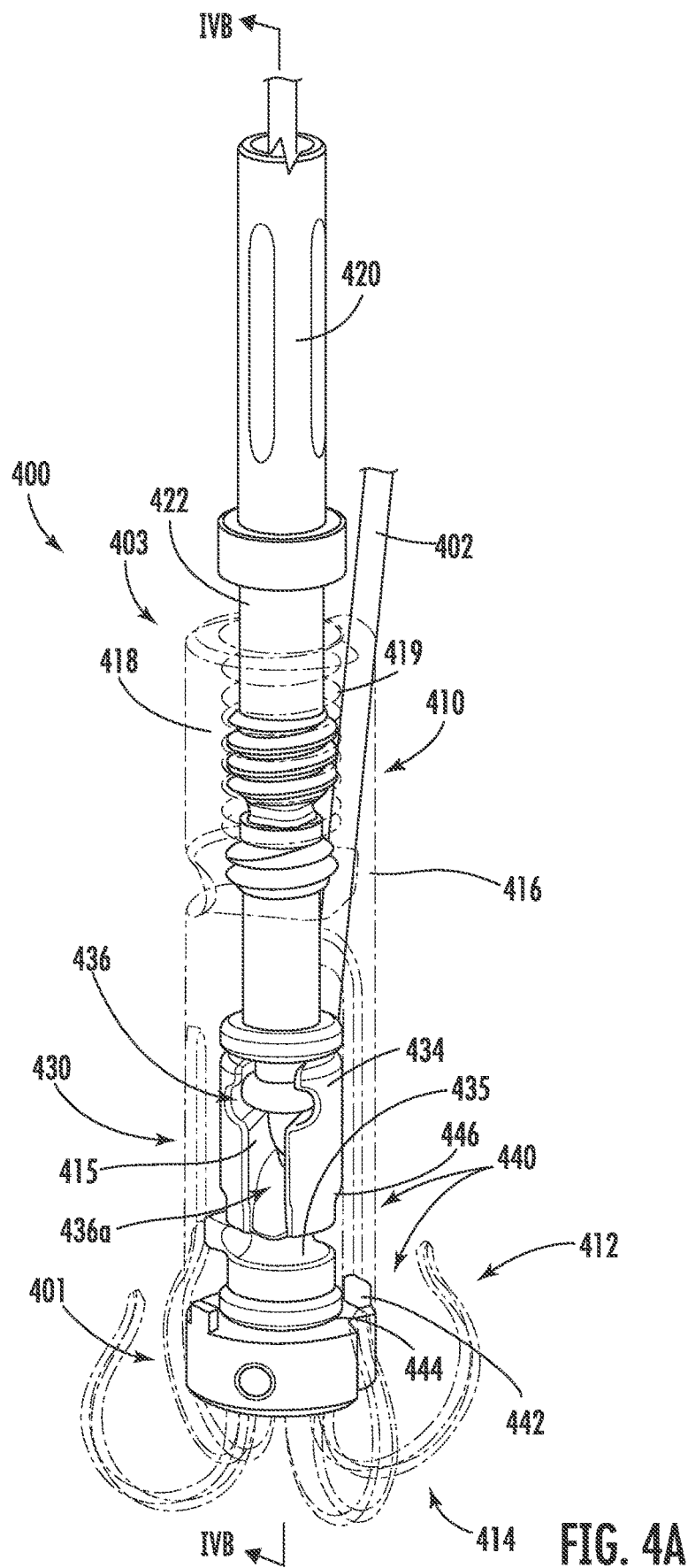
FIG. 4A is a perspective view of an artificial chordae tendineae tensioning and locking device formed in accordance with principles of the present disclosure with a housing portion in phantom.
Figure 4B:
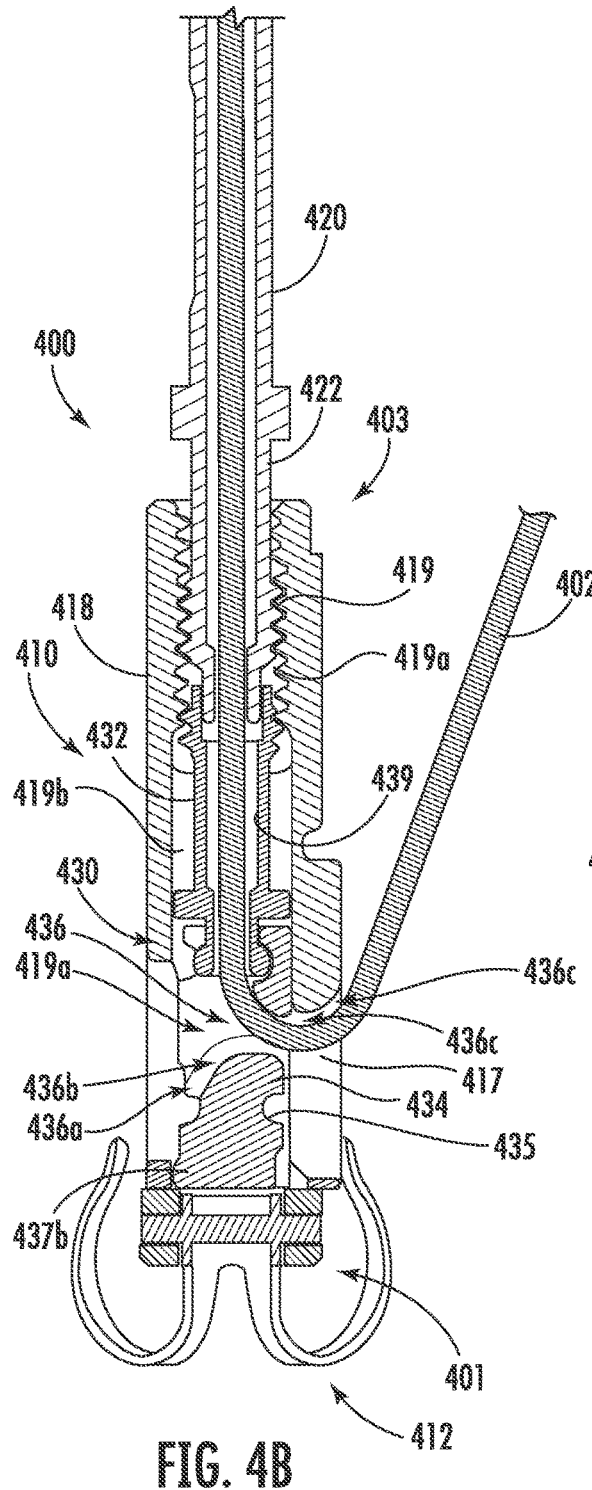
FIG. 4B is a cross-sectional view along line IVB-IVB of an artificial chordae tendineae tensioning and locking device as in FIG. 4A with a housing portion in phantom, and shown in an unlocked configuration.
Figure 4C:
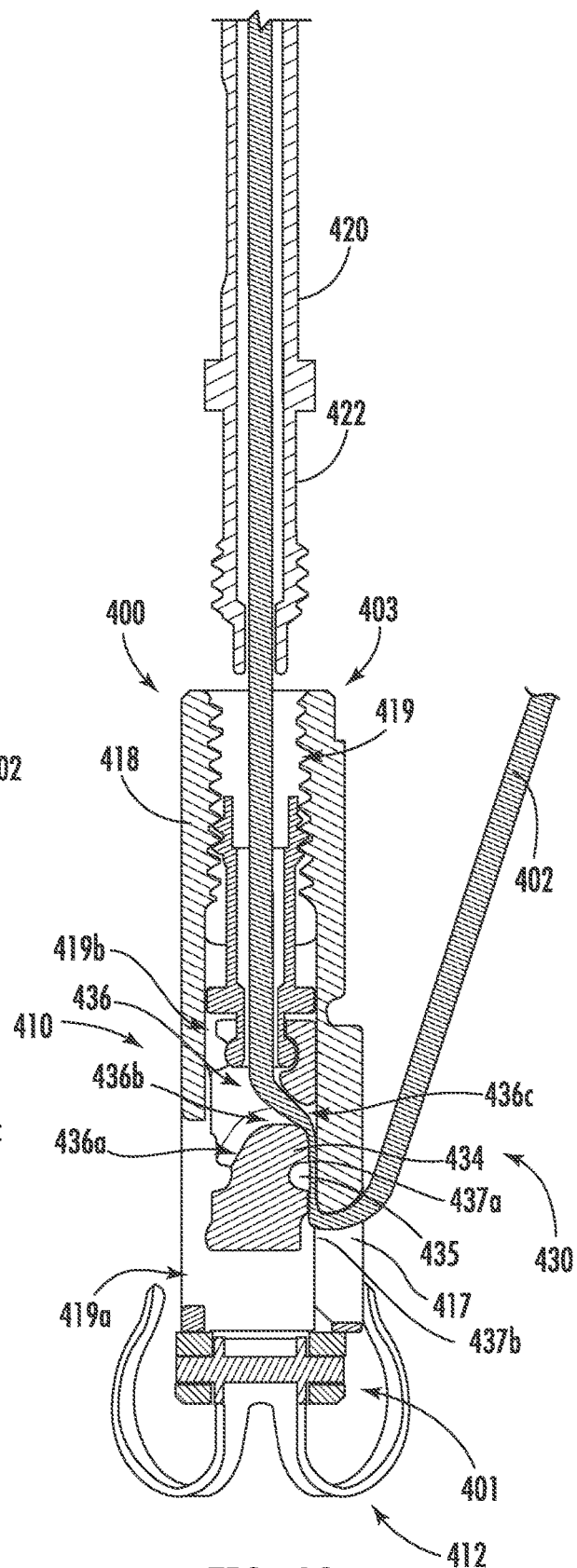
FIG. 4C is a cross-sectional view of an artificial chordae tendineae tensioning and locking device similar to that of FIG. 4B, but shown in a locked configuration.

An alternative configuration of a tensioning and locking device 400 with a locking assembly similar to the locking assembly 330 of the tensioning and locking device 300 of FIGS. 3A-3C, but having a different path along which the artificial chordae tendineae extends with respect to the carriage, is illustrated in FIGS. 4A-4C. The tensioning and locking device 400 may have an associated anchor 410, with a tissue-engaging portion 412, a body portion 414, and a locking portion 416, similar to the anchor 410 associated with the tensioning and locking device 300. For the sake of brevity and convenience, and without intent to limit, similar elements of the example of an embodiment illustrated in FIGS. 4A-4C with similar functions as in the example of an embodiment illustrated in FIGS. 3A-3C are indicated with the same reference characters differing in value by 100, reference being made to the above descriptions of those similar elements and functions and operations thereof.

The embodiment of FIGS. 4A-4C may be more suitable for use with a stiffer artificial chordae tendineae 402 than used in the embodiment of FIGS. 3A-3C. More particularly, the artificial chordae tendineae 402 may be inserted into position with respect to the locking assembly 430 by inserting the first and second free ends of the artificial chordae tendineae 402 through an entrance 415. One end of the artificial chordae tendineae 402 is extended through the longitudinal cavity 439 in the coupler 432 and through the stylet 422 and catheter 420. The other end of the artificial chordae tendineae 402 is extended through the carriage 434 (through a transverse pathway 436c therethrough) and out an exit 417 in the housing 418 substantially opposite the entrance 415. A ramped pathway 436a may guide the artificial chordae tendineae 402 from the entrance 415 to the longitudinal cavity 439 in the coupler 432 and/or to the transverse pathway 436c to exit through exit 417.

The longitudinal extent of the artificial chordae tendineae 402 through the longitudinal cavity 439 in the coupler 432 transitions along a connecting pathway 436b through the carriage 434 to the lateral extent of the artificial chordae tendineae 402 extending along the transverse pathway 436c and exiting through the exit 417 in the housing 418. The connecting pathway 436b may be angled with respect to the axial extent of the housing 418 to provide a relatively large radius of curvature for the transitioning of the direction of the artificial chordae tendineae 402 from the axial extent through the carriage 434 to the lateral extent out the exit 417.

As in the example of an embodiment illustrated in FIGS. 4A-4C, the carriage 434 of the locking assembly 430 has a round cross-section, similar to the carriage 334 of the locking assembly 330. The carriage 434 thus may similarly benefit from a clock feature 440 to inhibit rotation of the carriage 434 within the longitudinal cavity 419 of the housing 418. Also as in the example of an embodiment illustrated in FIGS. 3A-3C, the carriage 434 of the locking assembly 430 illustrated in FIGS. 4A-4C has a circumferential groove 435 across which the artificial chordae tendineae 402 extends (generally transverse or perpendicular) when the carriage 434 is shifted from the tension-adjusting region 419a to the locking region 419b of the longitudinal cavity 419 in the housing 418. The circumferential groove 435 may provide or define two pinch points 437a, 437b at which the artificial chordae tendineae 402 can be pinched between the carriage 434 and the locking region 419b of the longitudinal cavity 419 in the housing 418. As the carriage 434 moves from the tension-adjusting region 419a (in which relatively unrestricted movement of the artificial chordae tendineae 402 within the pathway 436 allows adjustment of tension of the artificial chordae tendineae 402) to the locking region 419b (e.g., towards the distal end 401 of the tensioning and locking device 400 in the illustrated example), the artificial chordae tendineae 402 becomes pinched between the pinch points 437a, 437b and the inner wall of the longitudinal cavity 419, thereby fixing the tension in the artificial chordae tendineae 402.

In the tensioning and locking devices 200, 300, 400, the locking assembly 230, 330, 430 includes a moveable element in the form of a carriage. The moveable element is moved with respect to the housing 218, 318, 418 of the tensioning and locking device 200, 300, 400 to shift the locking assembly 230, 330, 430 between a tension-adjusting configuration in which the artificial chordae tendineae 202, 302, 402 is selectively movable with respect to the locking assembly 230, 330, 430 (e.g., to allow adjustment of tension of the artificial chordae tendineae 202, 302, 402), and a tension-setting or locking configuration in which movement of the artificial chordae tendineae 202, 302, 402 with respect to the locking assembly 230, 330, 430 is inhibited or prevented (such terms being used interchangeably herein without intent to limit) to fix or set or lock (such terms being used interchangeably herein without intent to limit) the tension of the artificial chordae tendineae 202, 302, 402. It will be appreciated that a moveable element of a locking assembly 230, 330, 430 of a tensioning and locking device formed in accordance with principles of the present disclosure may have other configurations than as described with respect to the examples illustrated in FIGS. 2A-2D and FIGS. 3A-3C and FIGS. 4A-4C.

Figure 5A:
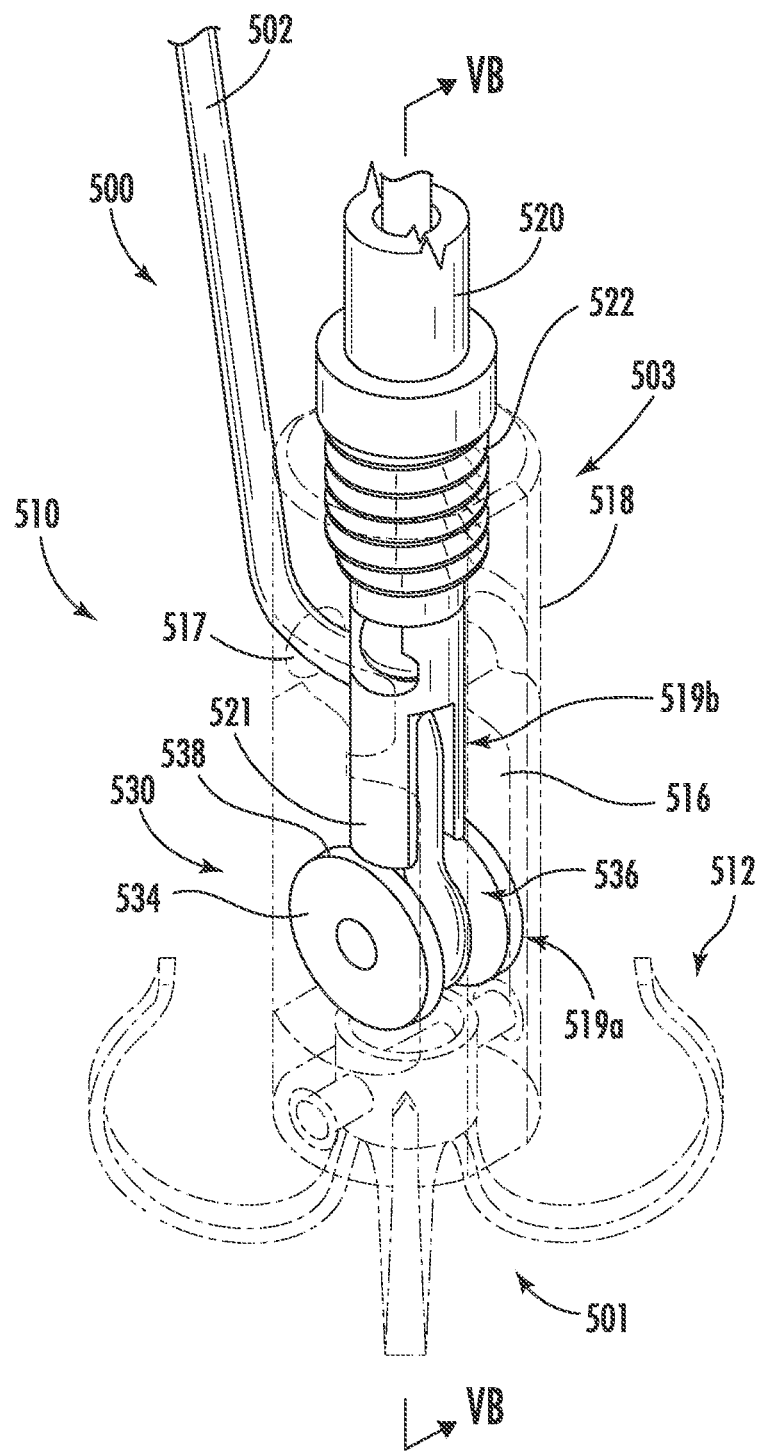
FIG. 5A is a perspective view of an artificial chordae tendineae tensioning and locking device formed in accordance with principles of the present disclosure with a housing portion in phantom.
Figure 5B:
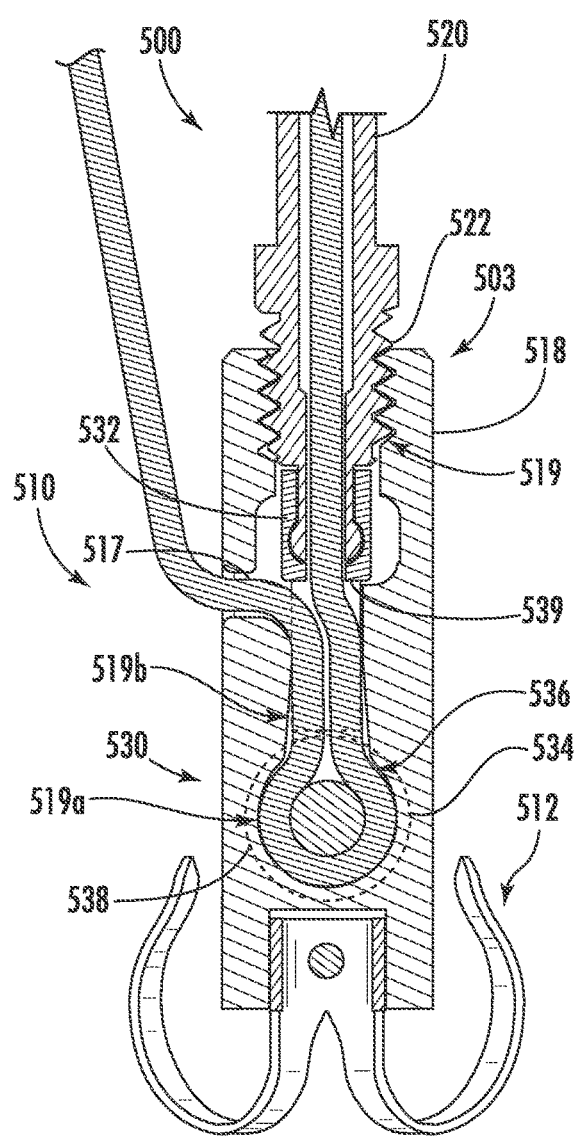
FIG. 5B is a cross-sectional view along line VB-VB of an artificial chordae tendineae tensioning and locking device as in FIG. 5A with a housing portion in phantom, and shown in an unlocked configuration.
Figure 5C:
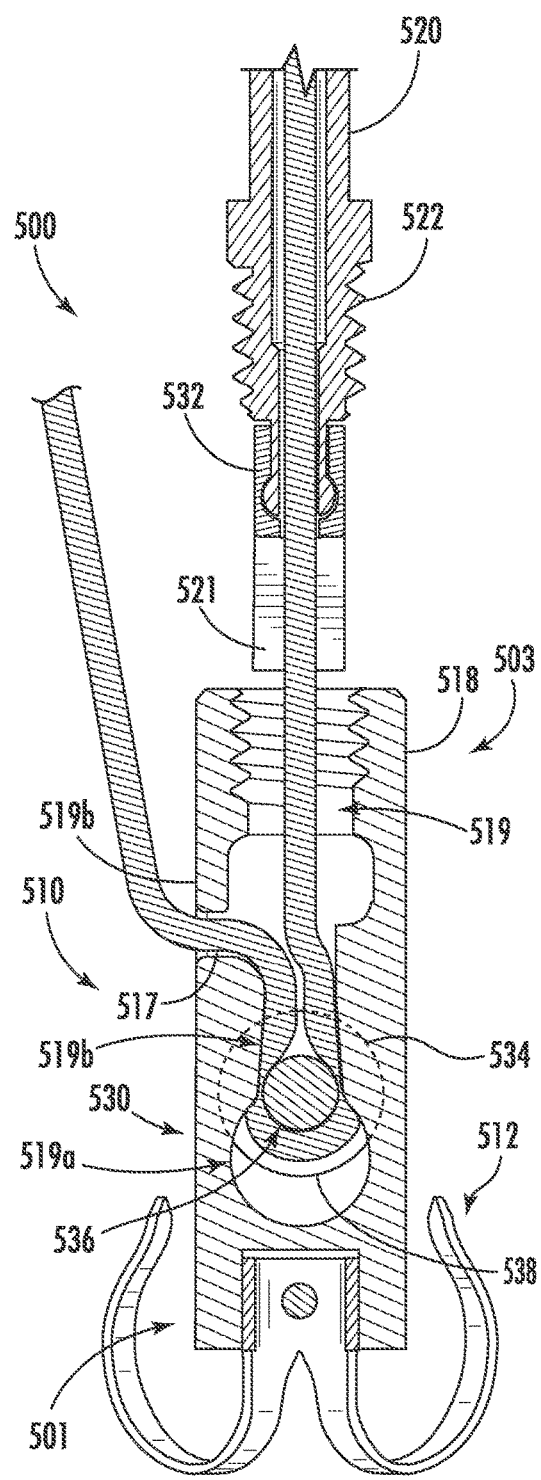
FIG. 5C is a cross-sectional view of an artificial chordae tendineae tensioning and locking device similar to that of FIG. 5B, but shown in a locked configuration.

In another example of a tensioning and locking device 500, illustrated in FIGS. 5A-5C, a locking assembly 530 may have a movable element in the form of a rolling element such as a roller 534. The rolling element rolls with movement of the artificial chordae tendineae 502 (such as during adjustment of the tension of the artificial chordae tendineae 502) and may be substantially cylindrical or substantially spherical. The locking assembly 530 of the tensioning and locking device 500 functions substantially the same as or similar to the locking assemblies 230, 330 of the tensioning and locking devices 200, 300, despite variations with regard to the configurations of the movable element and the housings. In particular, the artificial chordae tendineae 502 extends into the proximal end 503 of the tensioning and locking device 500 and into the longitudinal cavity 519 of the housing 518 to interact with the locking assembly 530, and exits the housing 518 via an exit 517 in the housing 518 to extend to be secured to a valve leaflet, in a similar manner as described above with reference to the tensioning and locking devices 200, 300. A moveable element of the locking assembly 530 is moved by an actuator, such as a stylet 522 at an end of a catheter 520, between a tension-adjusting region 519a and a locking region 519b within the housing 518 (e.g., between the proximal end 503 and distal end 501 of the tensioning and locking device 500). For the sake of brevity and convenience, and without intent to limit, similar elements as those in FIGS. 2A-2D and FIGS. 3A-3C and FIGS. 4A-4C with similar functions are indicated with the same reference characters differing in value by 100, reference being made to the above descriptions of those similar elements and functions and operations thereof. Although the locking and tension-adjusting functions of the tensioning and locking device 500 of FIGS. 5A-5C are substantially the same as or similar to the locking and tension-adjusting functions of the tensioning and locking devices 200, 300, 400 of FIGS. 2A-2D and FIGS. 3A-3C and FIGS. 4A-4C, respectively, because the moveable elements of the locking assemblies 230, 330, 430 differ in configuration, the functions thereof will be described in further detail.

With reference to FIG. 5B and FIG. 5C, it will be appreciated that the housing 518 of the tensioning and locking device 500 (which is illustrated in the example embodiment as being associated with an anchor 510 having a tissue-engaging portion 512, a body portion 514, and a locking portion 516) has a tension-adjusting region 519a having at least one dimension larger than a corresponding dimension (e.g., in substantially the same direction) of a locking region 519b. When the roller 534 is positioned in the tension-adjusting region 519a, the artificial chordae tendineae 502 may move substantially freely along a pathway 536 about the roller 534 (e.g., about a middle section of the roller 534) to allow for tension adjustment. When the roller 534 is moved into the locking region 519b, such as upon actuation of the stylet 522, the artificial chordae tendineae 502 is pinched or caught between the narrowed inner wall of the longitudinal cavity 519 and prevented from further movement, thereby setting the tension of the artificial chordae tendineae 502. Because the roller 534 may rotate as tension on the artificial chordae tendineae 502 is adjusted, the roller 534 is engaged by the stylet 522 (e.g., contacted by the stylet 522) such as by abutting a distal end 521 of the stylet 522 against ends 538 of the roller 534 (such as ends with larger diameters than the middle section about which the artificial chordae tendineae 502 extends, along a pathway 536) and straddling or otherwise not interfering with the artificial chordae tendineae 502 as it extends around the roller 534. The stylet 522 thus may retain the roller 534 in a particular position against tension from the artificial chordae tendineae 502 tending to pull the roller 534 proximally. In some embodiments, the distal end 521 extends from a coupler 532 rotatably coupled to a distal end of the stylet 522 such that rotation of the stylet 522 (to advance the stylet 522 distally towards the distal end 501 of the tensioning and locking device 500 or to retract the stylet 522 proximally towards the proximal end 503 of the tensioning and locking device 500) to adjust tension on the artificial chordae tendineae 502 does not cause rotation of the distal end 521 with respect to the roller 534. As the stylet 522 is actuated (such as by being withdrawn proximally) to set the tension on the artificial chordae tendineae 502, the roller 534 moves towards the locking region 519b (such as by being pulled by the tension the artificial chordae tendineae 502 extending around the roller 534) until the artificial chordae tendineae 502 is held between the roller 534 and the longitudinal cavity 519. As in the tensioning and locking devices 200, 300, 400 of FIGS. 2A-2D and FIGS. 3A-3C and FIGS. 4A-4C, respectively, the tensioning and locking device 500 of FIGS. 5A-5C allows for adjustment of tension on the artificial chordae tendineae 502 until the desired tension is achieved, at which point the tensioning and locking device 500 may be shifted into a tension-setting or locking configuration (such as by moving a locking element, such as the roller 534, of the locking assembly 530 into the locking region 519b), and the stylet 522 may be decoupled or removed from the tensioning and locking device 500.

Figure 6A:
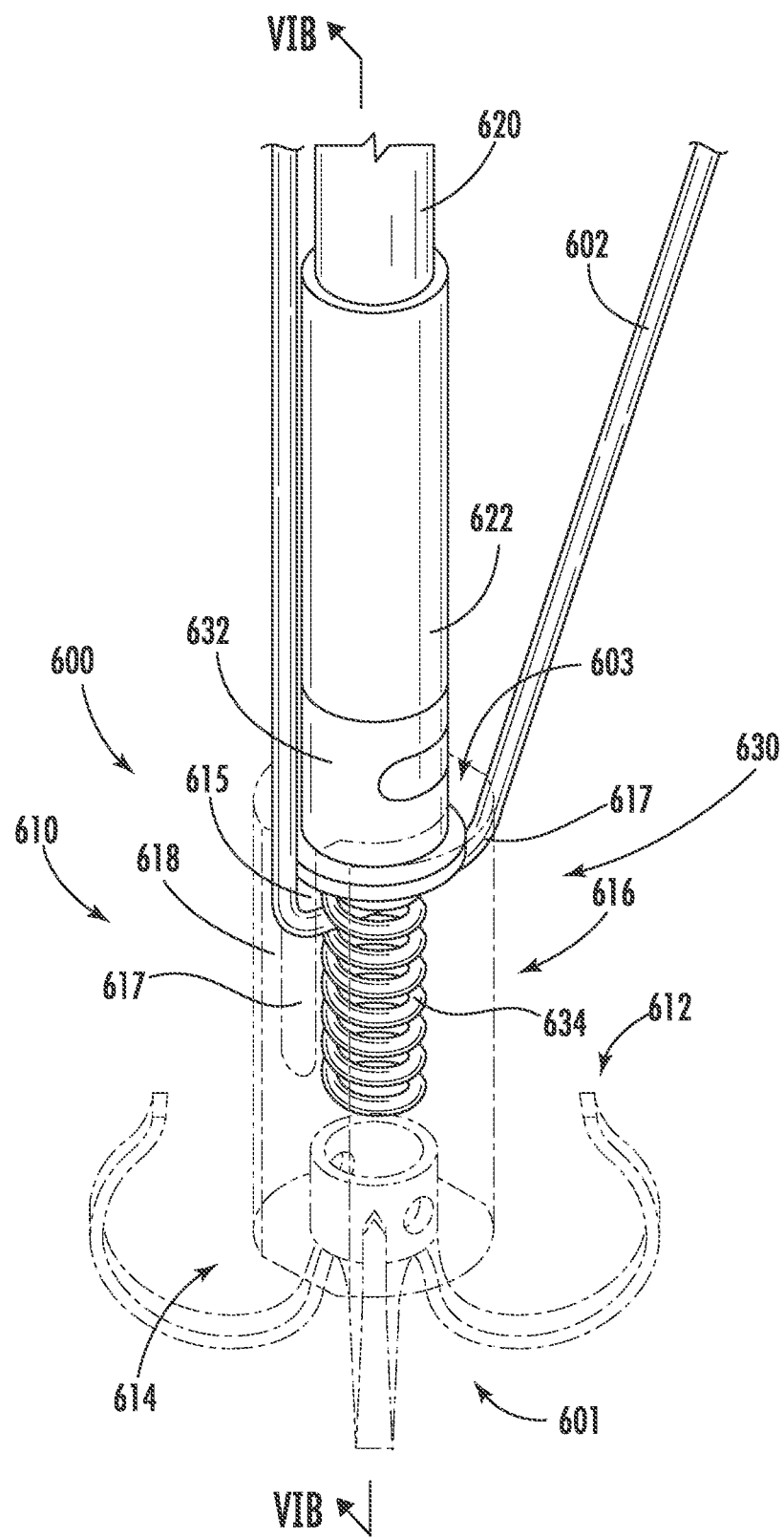
FIG. 6A is a perspective view of an artificial chordae tendineae tensioning and locking device formed in accordance with principles of the present disclosure.

The tensioning and locking device 600 of FIGS. 6A-6C has another configuration of a moveable element of a locking assembly 630 than those of the tensioning and locking devices 200, 300, 400, 500 of FIGS. 2A-2D, FIGS. 3A-3C, FIGS. 4A-4C, FIGS. 5A-5C, respectively. In particular, the moveable element of the locking assembly 630 of the tensioning and locking device 600 of FIGS. 6A-6C is in the form of a coil auger 634. For the sake of brevity and convenience, and without intent to limit, similar elements as those in FIGS. 2A-2D, FIGS. 3A-3C, FIGS. 4A-4C, FIGS. 5A-5C with similar functions are indicated with the same reference characters differing in value by 100, reference being made to the above descriptions of those similar elements and functions and operations thereof. Although the locking and tension-adjusting functions of the tensioning and locking device 600 of FIGS. 6A-6C are substantially the same as or similar to the locking and tension-adjusting functions of the tensioning and locking devices 200, 300, 400, 500 of FIGS. 2A-2D, FIGS. 3A-3C, FIGS. 4A-4C, FIGS. 5A-5C, respectively, because the moveable elements of the locking assemblies 230, 330, 430, 530, 630 differ in configuration, the functions will be described in further detail.

More particularly, with reference to FIGS. 6A-6C, and as may be more clearly appreciated with reference to FIG. 6B and FIG. 6C, the artificial chordae tendineae 602 extends laterally into a housing 618 of the tensioning and locking device 600 (which is illustrated in the example embodiment as being associated with an anchor 610 having a tissue-engaging portion 612, a body portion 614, and a locking portion 616), such as via an entrance 615. Instead of extending about the periphery or exterior of the movable element of the locking assembly 630, the artificial chordae tendineae 602 extends through the coils of the auger 634. As in the previously-described tensioning and locking devices 200, 300, the stylet 622 is coupled with the locking assembly 630 via a coupler 632. The coupler 632 may be fixed against axial movement (along the longitudinal axis LA of the tensioning and locking device 600) yet capable of rotating with respect to the housing 618 (e.g., a circumferential rib and groove engagement between the coupler 632 and the housing 618). Rotation of the stylet 622 (illustrated in this example of an embodiment as extending from a catheter 620) actuates the auger 634 to rotate, carrying the portion of the artificial chordae tendineae 602 proximally (towards proximal end 603 of the tensioning and locking device 600) or distally (towards the distal end 601 of the tensioning and locking device 600). In the tension-adjusting configuration, the artificial chordae tendineae 602 is free to move through the housing and through and across the auger 634. However, when the auger 634 is rotated to move the portion of the artificial chordae tendineae 602 extending therethrough away from the exit 617, the artificial chordae tendineae 602 is pinched between the auger 634 and the longitudinal cavity 619 within the housing 618 and into a locking position in which tension thereon is substantially fixed. In some embodiments, the entrance 615 is in the form of a slot permitting passage of the artificial chordae tendineae 602 therethrough without being pinched as the auger 634 is actuated or moved between the tension-adjusting configuration and the tension-setting or locking configuration.

Figure 6D:
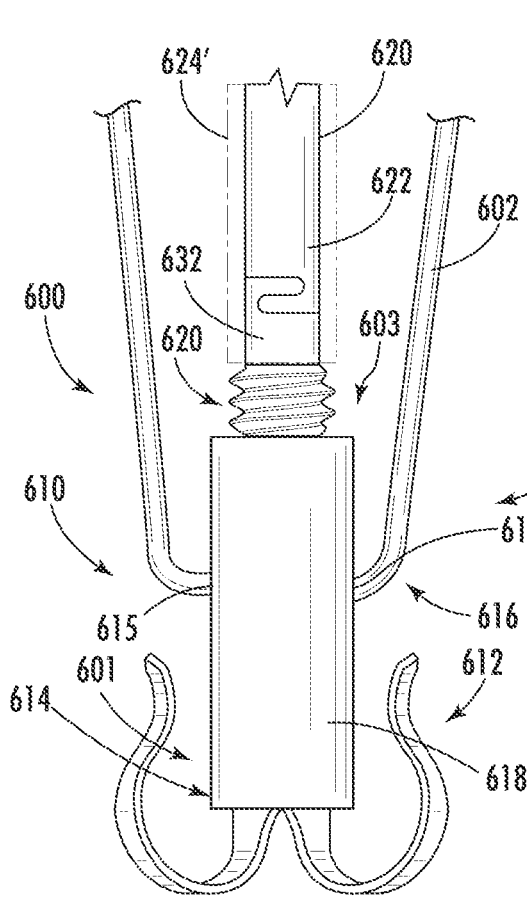
FIG. 6D is an elevational view of an artificial chordae tendineae tensioning and locking device as in FIGS. 6A-6C with an alternative configuration of an actuator.
Figure 6E:
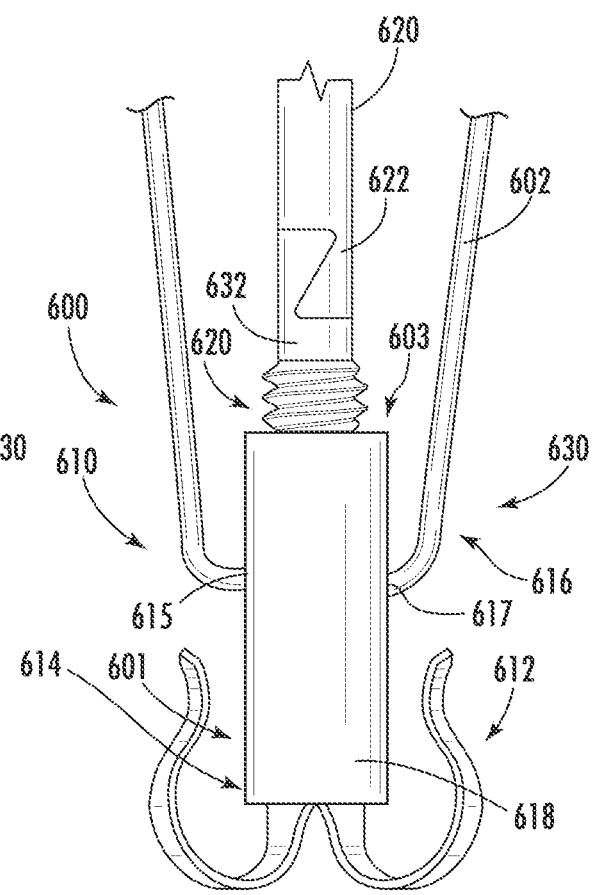
FIG. 6E is an elevational view of an artificial chordae tendineae tensioning and locking device as in FIGS. 6A-6D with an alternative configuration of an actuator.

To facilitate transference of rotational movement of the stylet 622 to the coupler 632, a railroad-car coupling may be used as illustrated. In particular, the stylet 622 and the coupler 632 may have ends shaped to interengage or interlock with each other to lock the stylet 622 and the coupler 632 against relative rotational movement. The stylet 622 and the coupler 632 may be fixed against relative movement causing disengagement of their interlocked ends (e.g., upon movement of the ends transverse to the longitudinal axes of the stylet 622 and coupler 632) through the use of a locking stylet 624 extending through lumens within the stylet 622 and the coupler 632, as illustrated in FIG. 6B. Alternatively, as illustrated in FIG. 6D, a locking stylet 624' extending over the stylet 622 and the coupler 632 may fix the stylet 622 and the coupler 632 against relative movement causing disengagement of their interlocked ends. Alternative shapes of the engaging locking ends of the stylet 622 and the coupler 632 are illustrated in FIG. 6E. It will be appreciated that the illustrated configurations are non-limiting examples, and other configurations are within the scope of the present disclosure.

Figure 7A:
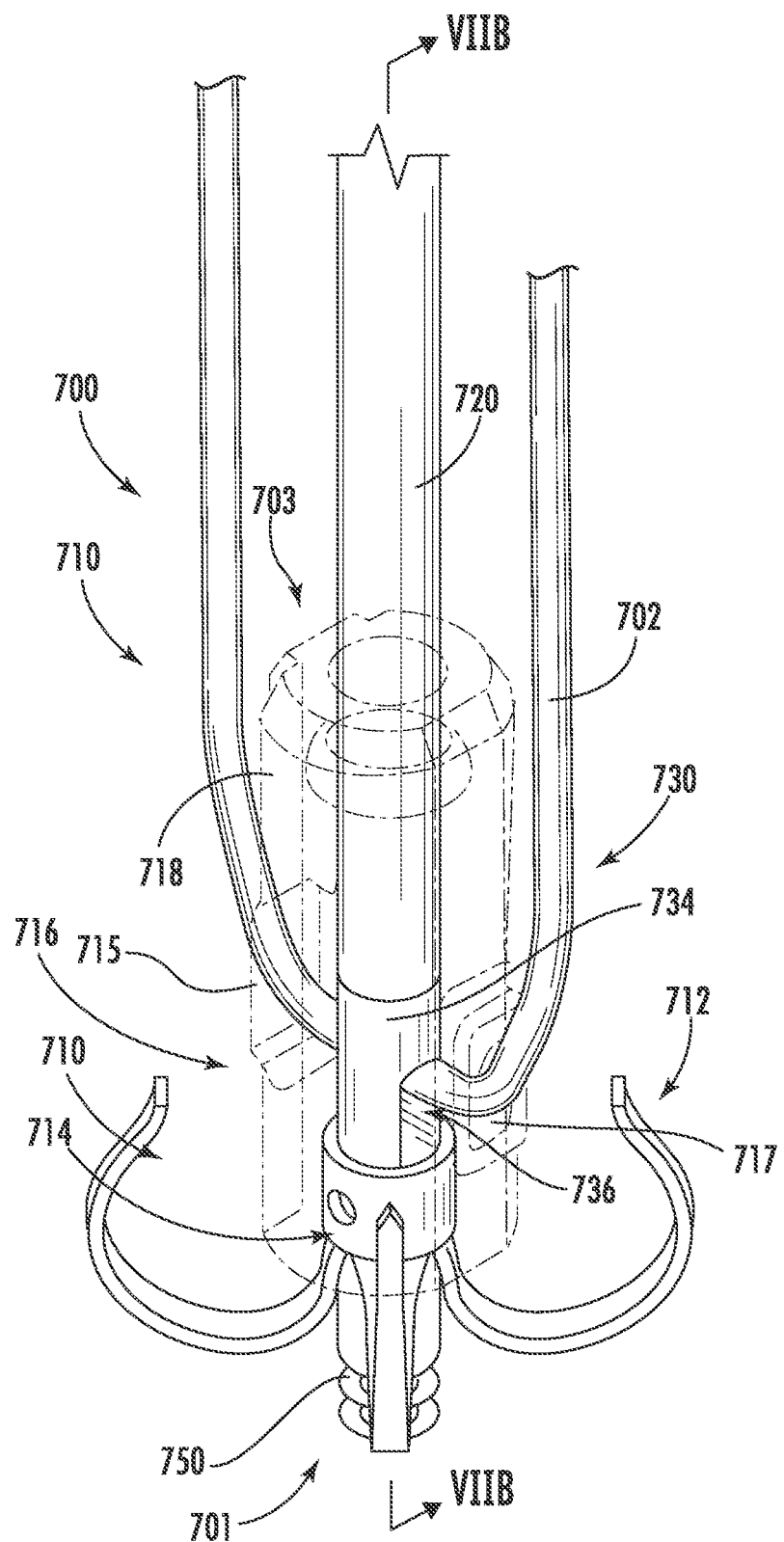
FIG. 7A is a perspective view, with elements in phantom, of an artificial chordae tendineae tensioning and locking device formed in accordance with principles of the present disclosure with an anchor portion in position in body tissue.
Figure 7B:
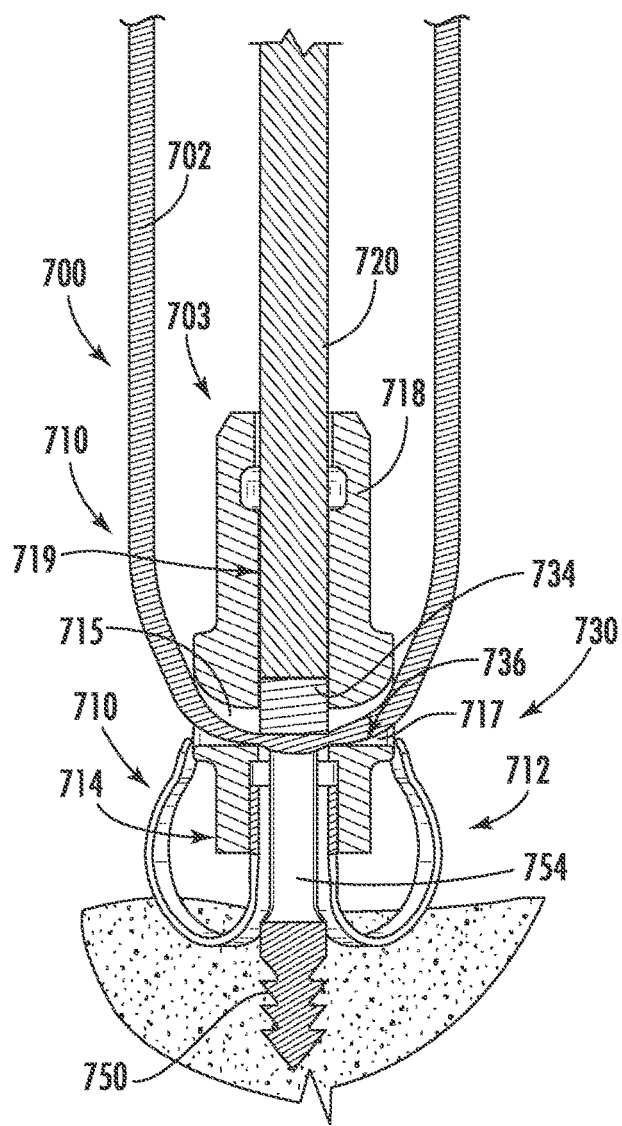
FIG. 7B is a cross-sectional view along line VIIB-VIIB of an artificial chordae tendineae tensioning and locking device as in FIG. 7A with a housing portion shown in phantom, and shown in a locked position in body tissue.
Figure 7C:
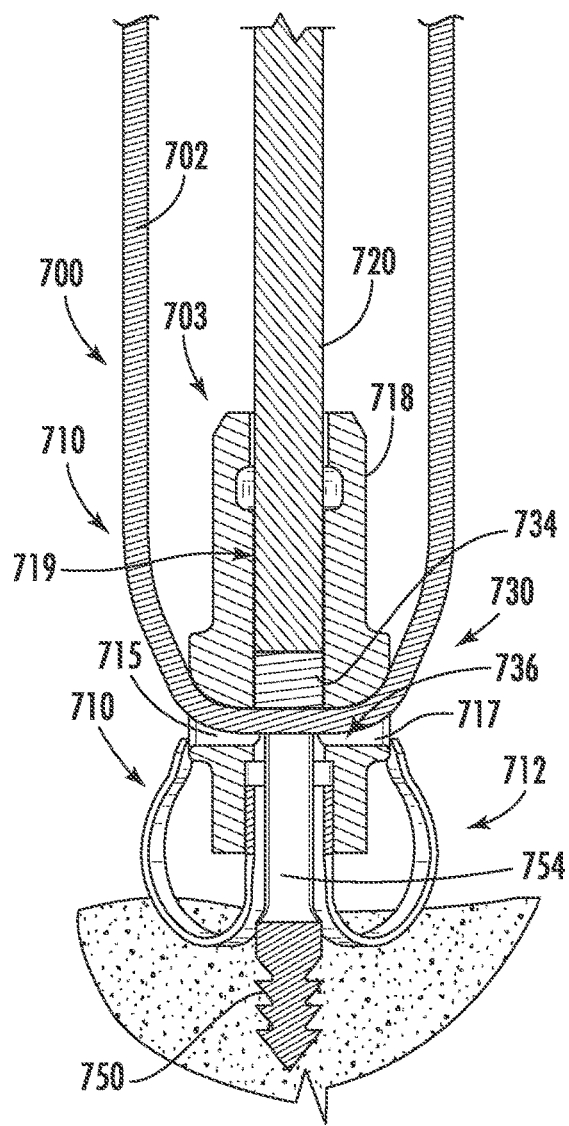
FIG. 7C is a cross-sectional view of an artificial chordae tendineae tensioning and locking device similar to that of FIG. 7B, but shown in an unlocked position in body tissue.

Another configuration of a moveable element of a locking assembly 730 is illustrated in FIGS. 7A-7C. For the sake of brevity and convenience, and without intent to limit, similar elements as those in FIGS. 2A-2D, FIGS. 3A-3C, FIGS. 4A-4C, FIGS. 5A-5C, FIGS. 6A-6C with similar functions are indicated with the same reference characters differing in value by 100, reference being made to the above descriptions of those similar elements and functions and operations thereof.

In the tensioning and locking device 700 of FIGS. 7A-7C, the moveable element of the locking assembly 730 includes a tissue-engaging movable element 734 configured to move with respect to the housing 718 of the tensioning and locking device 700 (which is illustrated in the example embodiment as being associated with an anchor 710 having a tissue-engaging portion 712, a body portion 714, and a locking portion 716). An actuator, such as in the form of an actuator shaft 720, extends through a longitudinal cavity 719 in the housing 718 to move the tissue-engaging movable element 734 (extending from the distal end 701 of the tensioning and locking device 700) between a tension-setting or locking configuration, in which tension on the artificial chordae tendineae 702 is substantially fixed, and a tension-adjusting configuration, in which tension on the artificial chordae tendineae 702 may be adjusted. More particularly, the artificial chordae tendineae 702 extends laterally into the housing 718 of the tensioning and locking device 700, such as via an entrance 715, to pass through the pathway 736 through (in this example, transversely through) the tissue-engaging movable element 734, and out of the housing 718 through the exit 717 to extend to a leaflet to which the artificial chordae tendineae 702 is secured. As may be appreciated upon comparison of FIG. 7B and FIG. 7C, when the tissue-engaging movable element 734 is engaged in tissue, as illustrated in FIG. 7B, the artificial chordae tendineae 702 may be pinched between an end of the pathway 736 and the end of either or both of the entrance 715 and the exit 717. Upon moving the shaft 722 proximally (towards the proximal end 703 of the tensioning and locking device 700), and also before the tissue-engaging movable element 734 is inserted a locking extent (as illustrated as in FIG. 7B) into the tissue, the artificial chordae tendineae 702 is no longer pinched (as illustrated in FIG. 7C), and tension therein may be adjusted as desired. In the illustrated embodiment, the entrance 715, the exit 717, and the pathway 736 are each elongated, such as to allow the artificial chordae tendineae 702 to be moved axially therein when the shaft 722 is moved axially. Other configurations are within the scope and spirit of the present disclosure, such as only the entrance 715 and the exit 717, or only the pathway 736 being elongated.

Although the tissue-engaging movable element 734 is illustrated in FIGS. 7A-7C with a spear-shaped tissue-engaging distal end 750, other configurations are within the scope of the present disclosure. For instance, the tissue-engaging movable element 734 may have a tissue-engaging distal end selectively movable between an insertion configuration and a tension-setting or locking configuration. For instance, a tissue-engaging distal end with movable arms, as illustrated in FIGS. 7D-7G, may be provided on a tissue-engaging movable element 734 such as provided in locking assembly 730 of the tensioning and locking device 700. In the embodiment illustrated in FIG. 7D and FIG. 7E, locking arms 752 may be formed integrally with (as a part of) a shaft portion 754. The locking arms 752 may be in an insertion configuration (e.g., flush with and/or matching the surrounding contour of the shaft portion 754), such as illustrated in FIG. 7D, when the tissue-engaging movable element 734 is inserted or secured or implanted into tissue, and may extend outwardly from the shaft portion 754 (e.g., pulled apart upon proximal movement of the shaft portion 754 once the tissue-engaging movable element 734 has been initially inserted into tissue) into an anchoring configuration, such as illustrated in FIG. 7E, to hold the tissue-engaging movable element 734 in place within the tissue. Alternatively, as illustrated in FIG. 7F and FIG. 7G, locking arms 752' may be formed separately from the shaft portion 754' and pivotably coupled thereto, such as via a pivot 755. The locking arms 752' may be in a compact insertion configuration (such as extending longitudinally along the shaft portion 754), as illustrated in FIG. 7F, when the tissue-engaging movable element 734 is inserted or secured or implanted into tissue, and may extend outwardly from the shaft portion 754 (e.g., pulled apart upon proximal movement of the shaft portion 754 once the tissue-engaging movable element 734 has been initially inserted into tissue) into an anchoring configuration, such as illustrated in FIG. 7G, to hold the tissue-engaging movable element 734 in place within the tissue. In some embodiment, the locking arms 752, 752' may be symmetrical. In some embodiments, more than one locking arm, such as two or more locking arms 752, 752' may be provided.

The devices, systems, and methods of the present disclosure may be used alone or together with other devices, systems, and methods to treat heart disease, such as, without limitation, with devices, systems, and methods as described in U.S. patent application Ser. No. 16/919,769, titled DEVICES, SYSTEMS, AND METHODS FOR ADJUSTABLY TENSIONING AN ARTIFICIAL CHORDAE TENDINEAE BETWEEN A LEAFLET AND A PAPILLARY MUSCLE OR HEART WALL; U.S. patent application Ser. No. 16/919,782, titled DEVICES, SYSTEMS, AND METHODS FOR CLAMPING A LEAFLET OF A HEART VALVE; U.S. patent application Ser. No. 16/919, 794, titled DEVICES, SYSTEMS, AND METHODS FOR ANCHORING AN ARTIFICIAL CHORDAE TENDINEAE TO A PAPILLARY MUSCLE OR HEART WALL; and U.S. patent application Ser. No. 16/919,806, titled DEVICES, SYSTEMS, AND METHODS FOR ARTIFICIAL CHORDAE TENDINEAE, each of which was filed on Jul. 2, 2020, and each of which is herein incorporated by reference in its entirety and for all purposes. Examples of devices described therein may be modified to incorporate embodiments or one or more features of the present disclosure. All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

Although embodiments of the present disclosure may be described with specific reference to mitral valves, a tensioning and locking device such as disclosed herein may be used in connection with repair or modification of any valve annulus, for example including a tricuspid valve annulus, and/or may similarly benefit any other dilatation, valve incompetency, valve leakage, and other similar heart failure conditions which involve anchoring a component to heart tissue. It will be further appreciated that although embodiments of tensioning and locking devices are described with respect to heart valve implant devices, the principles of the present disclosure may be applied to tensioning and locking devices used in connection with other types of devices used in the body, such as implanted in the body, particularly in areas with soft tissue and/or regular movement of the tissue in which the implant is located.

Although embodiments of the present disclosure may be described with specific reference to medical devices and systems (e.g., transluminal devices inserted through a femoral vein or the like) for selective access to heart tissue, it should be appreciated that such medical devices and systems may be used in a variety of medical procedures that require tensioning of a cord like element within the body. The disclosed medical devices and systems may also be inserted via different access points and approaches, e.g., percutaneously, endoscopically, laparoscopically, or combinations thereof.

It is to be understood by one of ordinary skill in the art that the present discussion is a description of illustrative examples of embodiments only, and is not intended as limiting the broader aspects of the present disclosure. The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. A system for adjusting tension in an artificial chordae tendineae extending between a leaflet of a heart valve and papillary muscle or a heart wall, the system comprising:
   a leaflet clip configured to be engaged with a leaflet of a heart valve and with the artificial chordae tendineae;
   an anchor configured to be engaged with a papillary muscle or heart wall;
   an artificial chordae tendineae extending between the leaflet clip and the anchor; and
   a locking assembly associated with the anchor and having a housing with a longitudinal axis and a locking element shaped with respect to the housing to be axially movable but not rotatable within the housing;
   wherein:

the artificial chordae tendineae extends through a pathway defined within the locking element of the locking assembly; and the locking element is configured to be selectively axially shiftable between a tension-adjusting configuration allowing the artificial chordae tendineae to move relative to the locking assembly to increase and decrease tension on the leaflet, and a tension-setting configuration inhibiting movement of the artificial chordae tendineae relative to the locking assembly to set tension on the leaflet.

2. The system of claim 1, wherein the locking element is movable within a longitudinal cavity defined in the housing to shift the locking assembly between the tension-adjusting configuration and the tension-setting configuration.

3. The system of claim 2, wherein the locking element comprises one of a carriage, a roller, an auger, or a tissue-engaging element movable axially within the longitudinal cavity in the housing.

4. The system of claim 2, wherein a pathway is defined along the movable locking element along which the artificial chordae tendineae extends axially.

5. The system of claim 4, wherein:
the longitudinal cavity in the housing defines a locking region and a tension-adjusting region;
the artificial chordae tendineae is movable with respect to the movable locking element when the movable locking element is within the tension-adjusting region;
an exterior portion of the pathway extends along an exterior of the movable locking element; and
one or more portions of the artificial chordae tendineae extending along the exterior portion of the pathway extending along the exterior of the movable locking element are pinched between the movable locking element and the tension-adjusting region when the movable locking element is within the locking region in the longitudinal cavity of the housing to set tension on the leaflet.

6. The system of claim 5, further comprising a stylet engageable with the movable locking element to move the movable locking element axially to shift the locking assembly between the tension-adjusting configuration and the tension-setting configuration.

7. The system of claim 6, further comprising a coupler configured to couple the stylet and the movable locking element, wherein the artificial chordae tendineae extends axially through the stylet, the coupler, and the movable locking element, and transversely through the movable locking element to the portion of the pathway extending along the exterior of the movable locking element, and transversely through the housing to the leaflet clip.

8. The system of claim 2, further comprising a stylet engageable with the movable locking element and rotatable to move the movable locking element axially to shift the locking assembly between the tension-adjusting configuration and the tension-setting configuration.

9. The system of claim 2, wherein:
the anchor comprises a body portion, a tissue-engaging portion extending distally from the body portion, and a locking portion extending proximally from the body portion; and
the housing is a portion of the locking portion of the anchor.

10. A device for adjusting tension of an artificial chordae tendineae, the device comprising:
an artificial chordae tendineae;
a housing defining a longitudinal cavity therein;

a locking assembly positioned in the housing and having an axially movable locking element having a pathway defined therethrough configured for passage of the artificial chordae tendineae therethrough, the locking element positioned within the longitudinal cavity of the housing and shaped with respect to the housing to not be rotatable within the housing, and to be axially movable within and with respect to the longitudinal cavity of the housing between a tension-adjusting configuration allowing the artificial chordae tendineae to move relative to the housing, and a tension-setting configuration inhibiting movement of the artificial chordae tendineae relative to the housing; and a coupler extending from the movable locking element and configured for engagement with an actuator for rotating to move the movable locking element axially but not rotatably with respect to the housing.

11. The device of claim 10, further comprising a tissue-engaging element configured to engage tissue of a heart to anchor an end of the artificial chordae tendineae with respect to the heart.

12. The device of claim 10, wherein the locking assembly comprises one of a carriage, a roller, an auger, or a tissue-engaging element.

13. The device of claim 10, wherein a pathway is defined along the movable locking element along which the artificial chordae tendineae extends axially.

14. The device of claim 13, wherein an interior portion of the pathway extends transversely through the movable locking element.

15. The device of claim 14, wherein an exterior portion of the pathway extends along an exterior of the movable locking element.

16. The system of claim 15, wherein:
the longitudinal cavity in the housing defines a locking region and a tension-adjusting region;
the artificial chordae tendineae is movable with respect to the movable locking element when the movable locking element is within the tension-adjusting region; and
one or more portions of the artificial chordae tendineae extending along the portion of the pathway extending along the exterior of the movable locking element are pinched between the movable locking element and the tension-adjusting region when the movable locking element is within the locking region to set tension on a leaflet.

17. The device of claim 13, wherein an exterior portion of the pathway extends along an exterior of the movable locking element.

18. A method of adjusting tension in an artificial chordae tendineae extending between a leaflet of a heart valve and papillary muscle or a heart wall, the method comprising:
extending the artificial chordae tendineae through a housing and a movable locking element of a locking assembly of the artificial chordae tendineae tensioning and locking device, the locking element shaped to move axially but not rotatably within the housing;
moving the artificial chordae tendineae relative to a housing of the locking assembly to increase or decrease tension on the leaflet when the locking assembly is in a tension-adjusting configuration; and
when a desired tension on the leaflet is reached, axially shifting, without rotating, the movable locking element of the locking assembly, with respect to the housing of the locking assembly, into a tension-setting configuration to set tension on the artificial chordae tendineae and on the leaflet.

19. The method of claim 18, wherein moving the artificial chordae tendineae relative to the housing further comprises coupling a stylet with the movable locking element of the locking assembly to move the movable locking element.

20. The method of claim 19, further comprising associating the artificial chordae tendineae with the movable locking element so that the artificial chordae tendineae is inhibited from moving relative to the housing when the locking assembly is in the tension-setting configuration.

* * * * *